United States Patent
Akitomi et al.

(10) Patent No.: US 9,454,642 B2
(45) Date of Patent: Sep. 27, 2016

(54) PREDICTION DEVICE, PREDICTION METHOD, PROGRAM, AND RECORDING MEDIUM

(75) Inventors: Jou Akitomi, Koto-ku (JP); Shintarou Katou, Koto-ku (JP); Shotaro Tsuji, Setagaya-ku (JP); Takashi Ohtsu, Yokohama (JP); Iwao Waga, Koto-ku (JP)

(73) Assignees: NEC Solution Innovators, Ltd., Tokyo (JP); KANAGAWA PREFECTURAL HOSPITAL ORGANIZATION, Kanagawa (JP)

( * ) Notice: Subject to any disclaimer, the term of this patent is extended or adjusted under 35 U.S.C. 154(b) by 134 days.

(21) Appl. No.: 13/807,876

(22) PCT Filed: Jul. 2, 2011
(Under 37 CFR 1.47)

(86) PCT No.: PCT/JP2011/065232
§ 371 (c)(1),
(2), (4) Date: Dec. 31, 2012

(87) PCT Pub. No.: WO2012/002549
PCT Pub. Date: Jan. 5, 2012

(65) Prior Publication Data
US 2013/0102480 A1 Apr. 25, 2013

(30) Foreign Application Priority Data
Jul. 2, 2010 (JP) .................................. 2010-152020

(51) Int. Cl.
| G01N 33/50 | (2006.01) |
| G06F 19/16 | (2011.01) |
| C12N 15/115 | (2010.01) |
| G06F 19/18 | (2011.01) |

(52) U.S. Cl.
CPC .............. *G06F 19/16* (2013.01); *C12N 15/115* (2013.01); *G06F 19/18* (2013.01); *C12N 2310/16* (2013.01)

(58) Field of Classification Search
None
See application file for complete search history.

(56) References Cited

U.S. PATENT DOCUMENTS

2005/0026217 A1* 2/2005 Saito .............................. 435/7.1

FOREIGN PATENT DOCUMENTS

| JP | 2763958 B2 | 6/1998 |
| WO | 91/19813 A1 | 12/1991 |

OTHER PUBLICATIONS

Zimmermann et al. Monitoring Genomic Sequences during SELEX Using High-Throughput Sequencing: Neutral SELEX. PLoS One 5(2): e9169, pp. 1-7.*
Chushak et al. Nucleic Acids Research, 2009, 1-9.*
Craig Tuerk et al., "Systematic Evolution of Ligands by Exponential Enrichment: RNA Ligands to Bacteriophage T4 DNA Polymerase", Science, 1990, pp. 505-510, vol. 249.
Michael Zuker "Mfold Web Server for Nucleic Acid Folding and Hybridization Prediction", Nucleic Acids Research, 2003, pp. 3406-3415, vol. 31, No. 13.
Andreas R. Gruber et al., "The Vienna RNA Websuite", Nucleic Acids Research, 2008, Web Server Issue, W70-W74, vol. 36.
Yaroslav Chushak et al., "In Silico Selection of RNA Aptamers", Nucleic Acids Research, 2009, pp. e87 (1-9), vol. 37, No. 12.
International Search Report of PCT/JP2011/065232 dated Aug. 23, 2011.

* cited by examiner

*Primary Examiner* — Michael Borin
(74) *Attorney, Agent, or Firm* — Sughrue Mion, PLLC

(57) ABSTRACT

The present invention provides a prediction device, a prediction method, a program, and a recording medium, with which whether or not desired aptamer sequences are enriched can be predicted easily. The prediction device of the present invention 10 includes an input unit 11, a calculation unit 12, and a prediction unit 13. The input unit 11 is a unit through which sequence information on a target aptamer sequence group including selected aptamers in a target pool and a reference aptamer sequence group including reference aptamer sequences are inputted. The calculation unit 12 calculates the free energy of the target aptamer sequence group and the free energy of the reference aptamer sequence group. The prediction unit 13 compares the free energy of these sequence groups, and predicts that the target pool is an enriched pool when the free energy of the target aptamer sequence group is lower than the free energy of the reference aptamer sequence group. The reference aptamer sequence group is a candidate aptamer sequence group including a plurality of candidate aptamer sequences or a virtual aptamer sequence group that is derived from the target aptamer sequence group and includes virtual aptamer sequences having the same base composition as the target aptamer sequence group.

7 Claims, 10 Drawing Sheets

PREDICTION DEVICE, PREDICTION METHOD, PROGRAM, AND RECORDING MEDIUM

CROSS REFERENCE TO RELATED APPLICATIONS

This application is a National Stage of International Application No. PCT/JP2011/065232 filed Jul. 2, 2011, claiming priority based on Japanese Patent Application No. 2010-152020 filed Jul. 2, 2010, the contents of all of which are incorporated herein by reference in their entirety.

TECHNICAL FIELD

The present invention relates to a prediction device, a prediction method, a program, and a recording medium, with which it is possible to predict whether or not desired aptamer sequences are enriched from a plurality of candidate aptamer sequences.

BACKGROUND ART

Aptamers are nucleic acid ligands that bind to their targets, and generally are produced by the SELEX (Systematic Evolution of Ligands by EXponential enrichment) method (Patent Document 1, Non-Patent Document 1). In the SELEX method, a plurality of rounds of selection process are performed, each of which includes the step of bringing a target into contact with an RNA library containing random sequences and the step of amplifying RNA bound to the target. Thus, sequences that can bind to the target are selected from an initial RNA library as desired aptamers.

Although an RNA pool is obtained in every round, the proportion of the desired aptamers in the pool of each round does not increase constantly as the round proceeds. Thus, the number of rounds generally is set based on the empirical rule of experimenters. However, if the number of rounds is set based on the empirical rule, the above-described selection process may be repeated even though a pool in which the desired aptamers are enriched is obtained already, for example. Also, for example, by repeating the above-described selection process a plurality of times, variations of RNAs contained in a pool are reduced. As a result, it appears that RNAs contained in the pool converge to desired aptamers (hereinafter this also is referred to as "enrichment"). However, there may be a case where the desired aptamers actually are not enriched in the pool of the final round. Thus, it is unknown how many rounds need to be performed in order to enrich the desired aptamers in the pool. Thus, from a practical standpoint, checking by a wet lab experiment is necessary, such as checking a pool of each round, checking the binding of RNAs taken as samples from each pool to the target, or checking the proportion of the RNA with verified bonding property to the target in the pool. As a result, there is a problem in that the SELEX method is not effective in terms of labor, time, and cost.

CITATION LIST

Patent Document(s)

Patent Document 1: Japanese Patent No. 2763958

Non-Patent Document(s)

Non-Patent Document 1: Science. (1990) 249, 505-510.

SUMMARY OF THE INVENTION

Problem to be Solved by the Invention

With the foregoing in mind, it is an object of the present invention to provide a prediction device, a prediction method, a program, and a recording medium, with which it is possible to predict whether or not desired aptamer sequences are enriched easily at the time of selecting the desired aptamer sequences from libraries.

Means for Solving Problem

In order to achieve the above object, the present invention provides a prediction device for predicting whether or not desired aptamer sequences are enriched in a target pool that contains selected aptamer sequences selected from a plurality of candidate aptamer sequences. The prediction device includes: an input unit; a free energy calculation unit; and a prediction unit for predicting whether or not desired aptamer sequences are enriched. The input unit is adapted to execute an input step of inputting sequence information on a target aptamer sequence group contained in the target pool and sequence information on a reference aptamer sequence group. The calculation unit is adapted to execute a calculation step of calculating a free energy of the target aptamer sequence group based on the sequence information on the target aptamer sequence group and a free energy of the reference aptamer sequence group based on the sequence information on the reference aptamer sequence group. The prediction unit is adapted to execute a prediction step of comparing the free energy of the target aptamer sequence group with the free energy of the reference aptamer sequence group and predicting that the desired aptamer sequences are enriched in the target pool when the free energy of the target aptamer sequence group is lower than the free energy of the reference aptamer sequence group. The reference aptamer sequence group is at least one of the following (1) and (2):

(1) a candidate aptamer sequence group including the plurality of candidate aptamer sequences; and
(2) a virtual aptamer sequence group that is derived from the target aptamer sequence group and includes virtual aptamer sequences having the same base composition as the target aptamer sequence group.

The present invention also provides a prediction method for predicting whether or not desired aptamer sequences are enriched in a target pool that contains selected aptamer sequences selected from a plurality of candidate aptamer sequences. The prediction method includes: a calculation step of calculating a free energy of the target aptamer sequence group based on the sequence information on the target aptamer sequence group contained in the target pool and a free energy of the reference aptamer sequence group based on the sequence information on the reference aptamer sequence group; and a prediction step of comparing the free energy of the target aptamer sequence group with the free energy of the reference aptamer sequence group and predicting that the desired aptamer sequences are enriched in the target pool when the free energy of the target aptamer sequence group is lower than the free energy of the reference aptamer sequence group. The reference aptamer sequence group is at least one of the following (1) and (2):

(1) a candidate aptamer sequence group including the plurality of candidate aptamer sequences; and
(2) a virtual aptamer sequence group that is derived from the target aptamer sequence group and includes virtual aptamer sequences having the same base composition as the target aptamer sequence group.

The present invention also provides a program that can execute the prediction method of the present invention on a computer.

The present invention also provides a recording medium having recorded thereon the program of the present invention.

Effects of the Invention

According to the present invention, it is possible to predict easily whether or not the desired aptamer sequences are enriched merely by comparing the free energy of the target aptamer sequence group with the free energy of the reference aptamer sequence group. Thus, for example, it is possible to prevent the selection process for enriching the desired aptamers from being repeated excessively or the number of the selection rounds for enrichment from being insufficient. Moreover, by predicting whether or not the enrichment has been achieved according to the present invention, checking by a wet lab experiment needs to be performed only with respect to a pool for which such checking is considered to be necessary, resulting in reduction in labor and cost, for example.

MODE FOR CARRYING OUT THE INVENTION

Figure 1A:
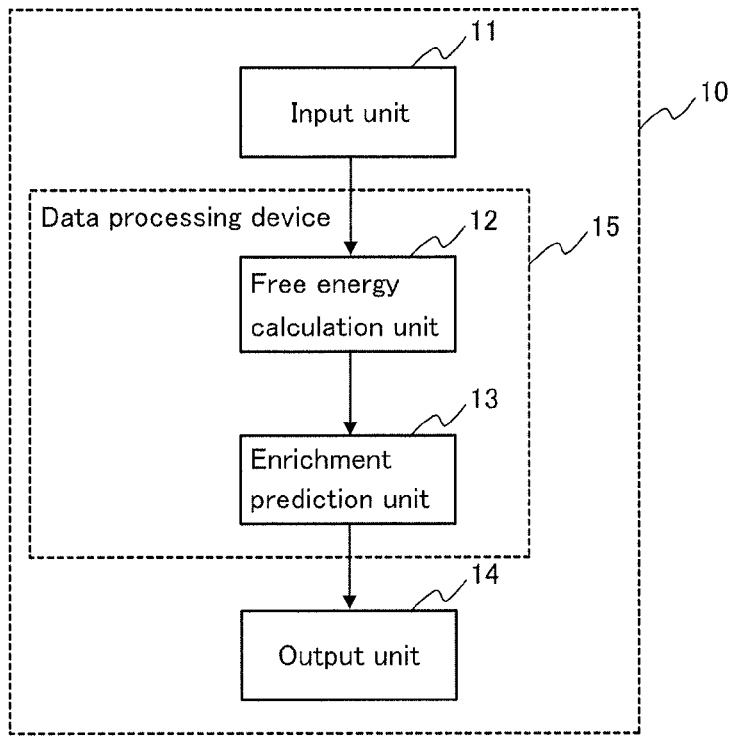
FIG. 1 shows block diagrams showing an embodiment of the prediction device according to the present invention.

The inventors of the present invention conducted a diligent study, and as a result, they found out that a pool in which desired aptamer sequences are enriched exhibits a lower free energy than a pool in which desired aptamer sequences are not enriched. As a result, the following prediction becomes possible: when free energies of any two pools are compared with each other and one of the pools exhibits a lower free energy than the other pool, desired aptamer sequences in the former pool are more enriched than those in the latter pool. The inventors of the present invention also found out that, when a virtual aptamer sequence group including virtual aptamer sequences having the same base composition as an aptamer sequence group contained in a pool is generated, if desired aptamer sequences are enriched in the pool, the aptamer sequence group contained in the pool exhibits a lower free energy than the virtual aptamer sequence group. As a result, the following prediction becomes possible: regarding an arbitrary pool, when the free energy of an aptamer sequence group contained in the pool is compared with the free energy of the virtual aptamer sequence group derived therefrom and found to be lower than the free energy of the virtual aptamer sequence group, the desired aptamer sequences are enriched in the pool.

In the present invention, the term "desired aptamer sequence" refers to a nucleic acid sequence that can bind to a given target. The term "candidate aptamer sequence" refers to a nucleic acid sequence whose binding property to the target is unknown, thus serving as a candidate for the desired aptamer sequence. The term "selected aptamer sequence" refers to an aptamer sequence satisfying a given condition among the candidate aptamer sequences. In the present invention, "enrichment of desired aptamer sequences" means that, for example, when aptamer sequences satisfying a given condition are selected from a pool $P_n$ containing a plurality of candidate aptamer sequences to obtain a pool $P_m$ containing the selected aptamer sequences, the proportion of the desired aptamer sequences in the pool $P_m$ after the selection (such a proportion also referred to as "the number of duplications") is higher than that in the pool $P_n$ prior to the selection. Also, "desired aptamer sequences are enriched" also can be referred to as "nucleic acid sequences contained in a pool converge to desired aptamer sequences", for example.

In the present invention, the term "target pool" refers to a pool to be subjected to prediction as to whether or not desired aptamer sequences are enriched therein, and this pool contains selected aptamer sequences selected from a plurality of candidate aptamer sequences. In the present invention, the term "target aptamer sequence group" refers to an aptamer sequence group including the selected aptamer sequences in the target pool, and hereinafter, it may also be referred to as a "selected aptamer sequence group", for example. The target aptamer sequence group may be a group including all the selected aptamer sequences contained in the target pool, or may be a group including some of them, for example.

In the present invention, the term "reference aptamer sequence group" refers to an aptamer sequence group to be compared with the target aptamer sequence group at the time of making the above-described prediction regarding the target pool. The reference aptamer sequence group will be described in detail below.

The present invention can be used for making the prediction in the following manner. First, screening is performed an arbitrary number of times (m times) with respect to a reference pool $P_n$ containing a plurality of candidate aptamer sequences to carry out selection from the candidate aptamer sequences. A target pool $P_{n+m}$ containing the selected candidate aptamer sequences (selected aptamer sequences) is then subjected to prediction as to whether or not desired aptamer sequences therein are more enriched than those in the reference pool $P_n$.

"n" in the reference pool $P_n$ indicates whether or not the pool $P_n$ has been subjected to selection by a given screening and the number of times the screening is performed (round), and is 0 or a positive integer. That is, for example, a pool $P_0$ (n=0) indicates a pool not yet subjected to a given screening and thus contains candidate aptamer sequences not yet subjected to selection; a pool $P_1$ (n=1) indicates a pool containing candidate aptamer sequences selected by subjecting the pool $P_0$ to a given screening one time, for example; and a pool $P_2$ (n=2) indicates a pool containing candidate aptamer sequences selected by subjecting the pool $P_1$ to a given screening one more time.

On the other hand, the pool $P_m$ indicates that the pool $P_m$ has been subjected to selection by subjecting the pool $P_n$ to a given screening m times, and m is a positive integer. That is, when n is 0 and m is 1, a pool $P_{n+m}=P_1$ is a pool containing selected aptamer sequence selected by subjecting a pool $P_0$, which is not yet subjected to a given screening and thus contains candidate aptamer sequences not yet subjected to selection, to a given screening one time. The given screening is not limited, and may be, for example, a selection process used in the SELEX method. The present invention is particularly useful for predicting whether or not desired aptamer sequences are enriched in a pool obtained in each round in the SELEX method.

As described above, the prediction device of the present invention is a prediction device for predicting whether or not desired aptamer sequences are enriched in a target pool that contains selected aptamer sequences selected from a plurality of candidate aptamer sequences. The prediction device includes: an input unit; a free energy calculation unit; and a prediction unit for predicting whether or not desired aptamer sequences are enriched. The input unit is adapted to execute an input step of inputting sequence information on a target aptamer sequence group contained in the target pool and sequence information on a reference aptamer sequence group. The calculation unit is adapted to execute a calculation step of calculating a free energy of the target aptamer sequence group based on the sequence information on the target aptamer sequence group and a free energy of the reference aptamer sequence group based on the sequence information on the reference aptamer sequence group. The prediction unit is adapted to execute a prediction step of comparing the free energy of the target aptamer sequence group with the free energy of the reference aptamer sequence group and predicting that the desired aptamer sequences are enriched in the target pool when the free energy of the target aptamer sequence group is lower than the free energy of the reference aptamer sequence group. The reference aptamer sequence group is at least one of the following (1) and (2): (1) a candidate aptamer sequence group including the plurality of candidate aptamer sequences; and (2) a virtual aptamer sequence group that is derived from the target aptamer sequence group and includes virtual aptamer sequences having the same base composition as the target aptamer sequence group.

The prediction device of the present invention may be configured so that, for example, the candidate aptamer sequence group (1) is used as the reference aptamer sequence group, and the prediction unit compares the calculated free energy of the target aptamer sequence group with a calculated free energy of the candidate aptamer sequence group and predicts that the desired aptamer sequences are enriched in the target pool when the free energy of the target aptamer sequence group is lower than the free energy of the candidate aptamer sequence group (1).

The prediction device of the present invention may be configured so that, for example, the virtual aptamer sequence group derived from the target aptamer sequence group (2) is used as the reference aptamer sequence group, and the prediction unit compares the calculated free energy of the target aptamer sequence group with a calculated free energy of the virtual aptamer sequence group (2) and predicts that the desired aptamer sequences are enriched in the target pool when the free energy of the target aptamer sequence group is lower than the free energy of the virtual aptamer sequence group (2).

The prediction device of the present invention may be configured so that, for example, it further includes a generation unit for generating the virtual aptamer sequences, and the generation unit is adapted to execute a generation step of generating the virtual aptamer sequence group (2) by generating the virtual aptamer sequences having the same base composition as the target aptamer sequence group based on the inputted sequence information on the target aptamer sequence group.

The prediction device of the present invention may be configured so that, for example, the candidate aptamer sequence group (1), the virtual aptamer sequence group (2), and a virtual aptamer sequence group (3) shown below are used as the reference aptamer sequence groups: (1) the candidate aptamer sequence group including the plurality of candidate aptamer sequences; (2) the virtual aptamer sequence group that is derived from the target aptamer sequence group and includes virtual aptamer sequences having the same base composition as the target aptamer sequence group; and (3) a virtual aptamer sequence group that is derived from the candidate aptamer sequence group and includes virtual aptamer sequences having the same base composition as the candidate aptamer sequence group, and the prediction unit executes the prediction step of: comparing the free energy of the target aptamer sequence group with the free energy of the virtual aptamer sequence group derived from the target aptamer sequence group (2); comparing the free energy of the candidate aptamer sequence group (1) with the free energy of the virtual aptamer sequence group derived from the candidate aptamer sequence group (3); and predicting that the desired aptamer sequences are enriched in the target pool when reduction of the free energy of the target aptamer sequence group relative to the free energy of the virtual aptamer sequence group derived from target aptamer sequence group (2) is greater than reduction of the free energy of the candidate aptamer sequence group (1) relative to the free energy of the virtual aptamer sequence group derived from the candidate aptamer sequence group (3).

The prediction device of the present invention may be configured so that, for example, it further includes: a generation unit for generating the virtual aptamer sequences, and the generation unit is adapted to execute a generation step of: generating the virtual aptamer sequence group (2) by generating the virtual aptamer sequences having the same base composition as the target aptamer sequence group based on the sequence information on the target aptamer sequence group; and generating the virtual aptamer sequence group (3) by generating the virtual aptamer sequences having the same base composition as the candidate aptamer sequence group based on the sequence information on the candidate aptamer sequence group.

In the prediction device of the present invention, the number of sequences in the virtual aptamer sequence group is from 100 to 10,000,000, for example.

In the prediction device of the present invention, the number of sequences in the target aptamer sequence group and the number of sequences in the candidate aptamer sequence group are both from 5 to 100,000,000, for example.

In the prediction device of the present invention, the free energy is at least one of a mean and a variance of free energies of the respective sequences, for example.

The prediction device of the present invention may be configured so that, for example, it further includes an output unit, and the output unit is adapted to output a result of prediction made by the prediction unit.

As described above, the prediction method of the present invention is a prediction method for predicting whether or not desired aptamer sequences are enriched in a target pool that contains selected aptamer sequences selected from a plurality of candidate aptamer sequences. The prediction method includes: a calculation step of calculating a free energy of the target aptamer sequence group based on the sequence information on the target aptamer sequence group contained in the target pool and a free energy of the reference aptamer sequence group based on the sequence information on the reference aptamer sequence group; and a prediction step of comparing the free energy of the target aptamer sequence group with the free energy of the reference aptamer sequence group and predicting that the desired aptamer sequences are enriched in the target pool when the free energy of the target aptamer sequence group is lower than the free energy of the reference aptamer sequence group. The reference aptamer sequence group is at least one of the following (1) and (2):

(1) a candidate aptamer sequence group including the plurality of candidate aptamer sequences; and
(2) a virtual aptamer sequence group that is derived from the target aptamer sequence group and includes virtual aptamer sequences having the same base composition as the target aptamer sequence group.

The prediction method of the present invention may be configured so that all the steps are executed on a computer.

The prediction method of the present invention may be configured so that, for example, the candidate aptamer sequence group (1) is used as the reference aptamer sequence group, and in the prediction step, the free energy of the target aptamer sequence group is compared with the free energy of the candidate aptamer sequence group (1), and when the free energy of the target aptamer sequence group is lower than the free energy of the candidate aptamer sequence group (1), it is predicted that the desired aptamer sequences are enriched in the target pool.

The prediction method of the present invention may be configured so that the virtual aptamer sequence group derived from the target aptamer sequence group (2) is used as the reference aptamer sequence group, and in the prediction step, the free energy of the target aptamer sequence group is compared with the free energy of the virtual aptamer sequence group (2), and when the free energy of the target aptamer sequence group is lower than the free energy of the virtual aptamer sequence group (2), it is predicted that the desired aptamer sequences are enriched in the target pool.

The prediction method of the present invention may be configured so that it further includes a generation step of generating virtual aptamer sequences, and the generation step is a step of generating the virtual aptamer sequence group (2) by generating the virtual aptamer sequences having the same base composition as the target aptamer sequence group based on the sequence information on the target aptamer sequence group.

The prediction method of the present invention may be configured so that the candidate aptamer sequence group (1), the virtual aptamer sequence group (2), and a virtual aptamer sequence group (3) shown below are used as the reference aptamer sequence groups:

(1) the candidate aptamer sequence group including the plurality of candidate aptamer sequences;
(2) the virtual aptamer sequence group that is derived from the target aptamer sequence group and includes virtual aptamer sequences having the same base composition as the target aptamer sequence group; and
(3) a virtual aptamer sequence group that is derived from the candidate aptamer sequence group and includes virtual aptamer sequences having the same base composition as the candidate aptamer sequence group.

The prediction step is a step of: comparing the free energy of the target aptamer sequence group with the free energy of the virtual aptamer sequence group derived from the target aptamer sequence group (2); comparing the free energy of the candidate aptamer sequence group (1) with the free energy of the virtual aptamer sequence group derived from the candidate aptamer sequence group (3); and predicting that the desired aptamer sequences are enriched in the target pool when reduction of the free energy of the target aptamer sequence group relative to the free energy of the virtual aptamer sequence group derived from target aptamer sequence group (2) is greater than reduction of the free energy of the candidate aptamer sequence group (1) relative to the free energy of the virtual aptamer sequence group derived from the candidate aptamer sequence group (3).

The prediction method of the present invention may be configured so that it further includes a generation step. The generation step is a step of: generating the virtual aptamer sequence group (2) by generating the virtual aptamer sequences having the same base composition as the target aptamer sequence group based on the sequence information on the target aptamer sequence group; and generating the virtual aptamer sequence group (3) by generating the virtual aptamer sequences having the same base composition as the candidate aptamer sequence group based on the sequence information on the candidate aptamer sequence group.

In the prediction method of the present invention, the number of sequences in the virtual aptamer sequence group is from 100 to 10,000,000, for example.

In the prediction method of the present invention, the number of sequences in the target aptamer sequence group and the number of sequences in the candidate aptamer sequence group are both from 5 to 100,000,000, for example.

In the prediction method of the present invention, the free energy is at least one of a mean value and a variance value, for example.

The program according to the present invention can execute the prediction method of the present invention on a computer.

The recording medium according to the present invention has recorded thereon the program according to the present invention.

More specific embodiments of the present invention will be described with reference to the accompanying drawings.

It is to be noted, however, that the present invention is by no means limited to the following embodiments.

Embodiment 1

The present embodiment is directed to an example where the candidate aptamer sequence group (1) is used as the reference aptamer sequence group. The candidate aptamer sequence group includes a plurality of candidate aptamer sequences.

According the present embodiment, for example, when a pool $P_n$ containing the plurality of candidate aptamer sequences is subjected to selection to obtain a pool $P_{n+m}$ containing the thus-selected aptamer sequences, it is possible to predict whether or not the desired aptamer sequences in the pool $P_{n+m}$ are more enriched than those in the pool $P_n$.

In the present embodiment, the pool $P_n$ containing the plurality of candidate aptamer sequences is referred to as a "reference pool" or "candidate pool" to be compared with the target pool. The reference aptamer sequence group, i.e., the candidate aptamer sequence group is a group including any candidate aptamer sequences among the candidate aptamer sequences in the candidate pool. The candidate aptamer sequence group may be a group including all the candidate aptamer sequences in the candidate pool, or may be a group including some of them.

The target pool $P_{n+m}$ is a pool containing the selected aptamer sequences selected from the plurality of candidate aptamer sequences and also is referred to as a "selected pool". The target aptamer sequence group is a group including any selected aptamer sequences among the selected aptamer sequences in the target pool, and also is referred to as a "selected aptamer sequence group". The target aptamer sequence group may be a group including all the selected aptamer sequences in the target pool, or may be a group including some of them.

Hereinafter, in the present embodiment, the reference aptamer sequences also are referred to as "candidate aptamer sequences", the reference aptamer sequence group also is referred to as a "candidate aptamer sequence group", the target aptamer sequences also are referred to as "selected aptamer sequences", and the target aptamer sequence group also is referred to as a "selected aptamer sequence group".

FIG. 1A shows an example of the configuration of the prediction device according to the present embodiment. As shown in FIG. 1A, a prediction device 10 includes an input unit 11, a free energy calculation unit 12, an enrichment prediction unit 13, and an output unit 14. The free energy calculation unit 12 and the enrichment prediction unit 13 may be incorporated in a data processing device 15, which is hardware, for example, as shown in FIG. 1A. The data processing device 15 may include CPU and the like, for example.

The input unit 11 is connected electrically to the free energy calculation unit 12, for example. The free energy calculation unit 12 is connected electrically to the enrichment prediction unit 13, for example. The enrichment prediction unit 13 is connected electrically to the output unit 14, for example.

Figure 1B:
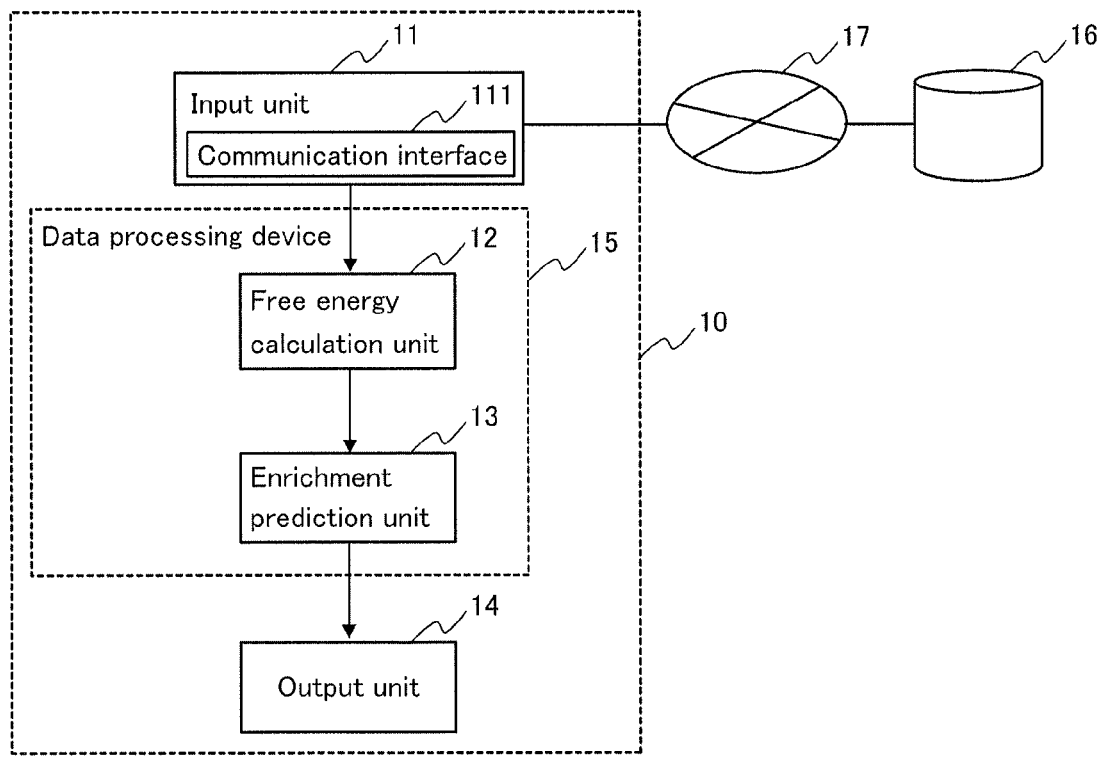

The input unit 11 is a unit through which sequence information on the candidate aptamer sequence group (the reference aptamer sequence group) and sequence information on the selected aptamer sequence group (the target aptamer sequence group) are inputted to the free energy calculation unit 12. The input unit 11 is not particularly limited, and examples thereof include: input devices generally included in computers, such as a keyboard and a mouse; input files; and other computers. As shown in FIG. 1B, the input unit 11 may be a unit for reading out the sequence information on the candidate aptamer sequence group and the selected aptamer sequence group, which is stored in a database, for example. In this case, for example, as shown in FIG. 1B, the sequence information previously stored in a server 16 is read out by the input unit 11 through a line network 17. The input unit 11 may include, for example, a communication interface 111, as shown in FIG. 1B. In FIG. 1B, the same components as those in FIG. 1A are given the same reference numerals.

The number of aptamer sequences on which sequence information is to be inputted through the input unit 11 is not particularly limited. As the sequence information on the candidate aptamer sequence group, for example, sequence information on all the candidate aptamer sequences contained in the reference pool may be inputted, or sequence information on some of the candidate aptamer sequences may be inputted. Also, as the sequence information on the selected aptamer sequence group, for example, sequence information on all the selected aptamer sequences contained in the target pool may be inputted, or sequence information on some of the selected aptamer sequences may be inputted. Specifically, the number of sequences in each of the candidate aptamer sequence group and the selected aptamer sequence group on which sequence information is to be inputted through the input unit 11 is 5 to 100,000,000, preferably 10 to 100,000, and more preferably 20 to 200, for example.

The enrichment of the desired aptamer sequences generally can be carried out by performing a plurality of rounds of screening with respect to an aptamer sequence library. Thus, in this enrichment process, an initial pool (round 0) before starting screening and pools of the respective rounds are obtained, for example. In the present invention, for example, from the initial pool not yet subjected to the screening and the pools of the respective rounds having subjected to the screening, pools can be selected and set as the reference pool and the target pool. The pool of any round can be set as the reference pool $P_n$. Since the target pool $P_{n+m}$ is a pool containing the selected aptamer sequences selected as described above, a pool of a round subsequent to the round of the reference pool can be set as the target pool $P_{n+m}$, for example. In the reference pool $P_n$ and the target pool $P_{n+m}$, n and m each indicate the number of times the screening has been performed (i.e., round). n is 0 or a positive integer, and m is a positive integer. Specifically, as the reference pool $P_n$ it is possible to set a pool $P_0$ (round n=0) not yet subjected to the screening or a pool $P_{n \geq 1}$ (round n≥1) having subjected to the screening at least one time, for example. On the other hand, as the target pool $P_{n+m}$, it is possible to set a pool $P_{n+m}$ of a round n+m (n is 0 or a positive integer, and m is a positive integer), which has been further subjected to the screening m times after the round n, for example. When the reference pool is the pool $P_0$ of the round 0, it is possible to set, as the target pool $P_{n+m}$, a pool $P_{m \geq 1}$ of a round subsequent to the round 0, specifically, the pool $P_1$ of the round 1 and/or the pool $P_{m \geq 2}$ of a round subsequent to the round 1, for example.

In the present embodiment, for example, not only sequence information on aptamer sequences in each of two kinds of pools of any different rounds set as the reference pool and the target pool but also sequence information on aptamer sequences in at least one pool of any other different round may be inputted. Alternatively, for example, sequence information on aptamer sequences in pools of all the rounds may be inputted. In these cases, for example, the reference pool and the target pool may be set after the input of the sequence information, and then, the free energies of the respective pools may be calculated as will be described below. Alternatively, for example, the reference pool and the target pool may be set after the calculation of free energies of the pools of the respective rounds on which sequence information has been inputted, and then, the free energy of the target pool may be compared with the free energy of the reference pool as will be described below. As described above, sequence information to be inputted regarding each pool may be sequence information on all the aptamer sequences contained therein or on some of them, for example.

The sequence information on each of the candidate aptamer sequences and the selected aptamer sequences may be sequence information on aptamers actually produced by a wet lab experiment or on aptamers designed by a dry lab experiment (in silico), for example. Specifically, in the case where the candidate aptamer sequences are sequences of aptamers produced by a wet lab experiment, for example, aptamers selected from the candidate aptamers by a wet lab experiment based on a given condition can be set as selected aptamers, and information on the sequences of these aptamers can be set as sequence information on the selected aptamer sequences. The method for selecting aptamers by a wet lab experiment is not particularly limited, and can be a SELEX method, for example. On the other hand, in the case where the candidate aptamer sequences are sequences of aptamers designed in silico, for example, aptamer sequences selected from the candidate aptamer sequences in silico based on a given condition can be set as the selected aptamer sequences. The method for selecting the aptamer sequences in silico is not particularly limited, and can be, for example, selecting aptamer sequences having a given feature from the candidate aptamer sequences based on the sequence information thereon. The feature is not particularly limited, and can be set as appropriate. Examples of the feature include the arrangement of bases, the appearance frequency of each base, the putative secondary structure, the content of each base, the appearance frequency of successive bases, the presence or absence of a motif sequence, and the melting temperature.

The free energy calculation unit 12 calculates the free energy of the candidate aptamer sequence group from the inputted sequence information on the candidate aptamer sequence group in the reference pool, and calculates the free energy of the selected aptamer sequence group from the inputted sequence information on the selected aptamer sequence group in the target pool. The free energy of the candidate aptamer sequence group also can be referred to as the free energy of the reference pool, for example. The free energy of the selected aptamer sequence group also can be referred to as the free energy of the target pool, for example. The free energy can be calculated from the inputted sequence information, for example. The free energy can be calculated based on: sequence information on the sequences, such as the arrangement of bases, the putative secondary structure, and the content of each base; and solvent information such as the temperature and the salt concentration, for example. The calculation method is not particularly limited. The calculation can be carried out by a conventionally known method, examples of which include: a method utilizing free energy minimization with the use of Mfold (M. Zuker, Mfold web server for nucleic acid folding and hybridization prediction. Nucleic Acids Res. 31 (13), 3406-15, 2003) or RNAfold (Andreas R Gruber et al., The vienna rna websuite. Nucleic Acids Res, 36 (Web Server issue):

W70-W74, July 2008). The free energy preferably is a minimum free energy (MFE), for example.

The free energy of the candidate aptamer sequence group may be, for example, the mean or variance of the free energies of the respective candidate aptamer sequences included in the candidate aptamer sequence group. Specifically, based on the inputted sequence information on the plurality of candidate aptamer sequences, the free energies of the respective candidate aptamer sequences are calculated, and further, the mean or variance of the thus-calculated free energies is calculated, which may be set as the mean or the variance of the free energies in the candidate aptamer sequence group. Similarly, the free energy of the selected aptamer sequence may be, for example, the mean or the variance of the free energies of the respective selected aptamer sequences included in the selected aptamer sequence group. Specifically, based on the inputted sequence information on the plurality of selected aptamer sequences, the free energies of the respective selected aptamer sequences are calculated, and further, the mean or variance of the thus-calculated free energies is calculated, which may be set as the mean or the variance of the free energies in the selected aptamer sequence group. The number of the candidate aptamer sequences and the number of the selected aptamer sequences to be subjected to free energy calculation are not particularly limited, and each may be, for example, 5 to 100,000,000, preferably 10 to 100,000, and more preferably 20 to 200.

The enrichment prediction unit 13 retrieves the free energy information from the free energy calculation unit 12 and compares the free energy of the selected aptamer sequence group in the target pool with the free energy of the candidate aptamer sequence group in the reference pool. Then, when the free energy of the selected aptamer sequence group is lower than the free energy of the candidate aptamer sequence group, the enrichment prediction unit 13 predicts that the desired aptamer sequences are enriched in the target pool. That is, it can be predicted that the desired aptamers in the target pool are more enriched than those in the reference pool.

It is preferable to predict that the desired aptamer sequences are enriched in the target pool when, for example, the free energy of the selected aptamer sequence group in the target pool is significantly lower than the free energy of the candidate aptamer sequence group in the reference pool, because this improves the reliability of the results of prediction. The method for determining whether or not the difference between these free energies is significant is not particularly limited, and examples thereof include the t test and the K-S test. For example, in the case of the t test, it can be determined that the difference is significant with the significance level of 5% (P=0.05).

The output unit 14 is not particularly limited as long as it is a unit that outputs the results of prediction made by the enrichment prediction unit 13. The output unit 14 is not particularly limited, and examples thereof include: output devices generally included in computers, such as a display device and a printer; output files; and other computers.

Figure 2:
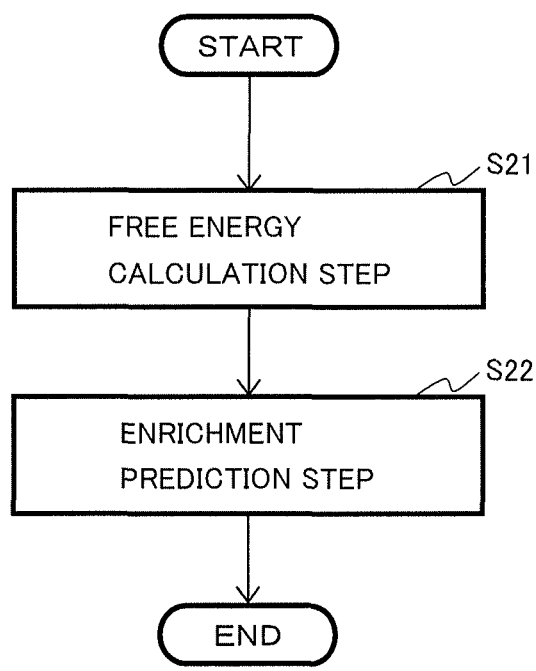
FIG. 2 is a flowchart illustrating an embodiment of the prediction method and prediction program according to the present invention.
Figure 3:
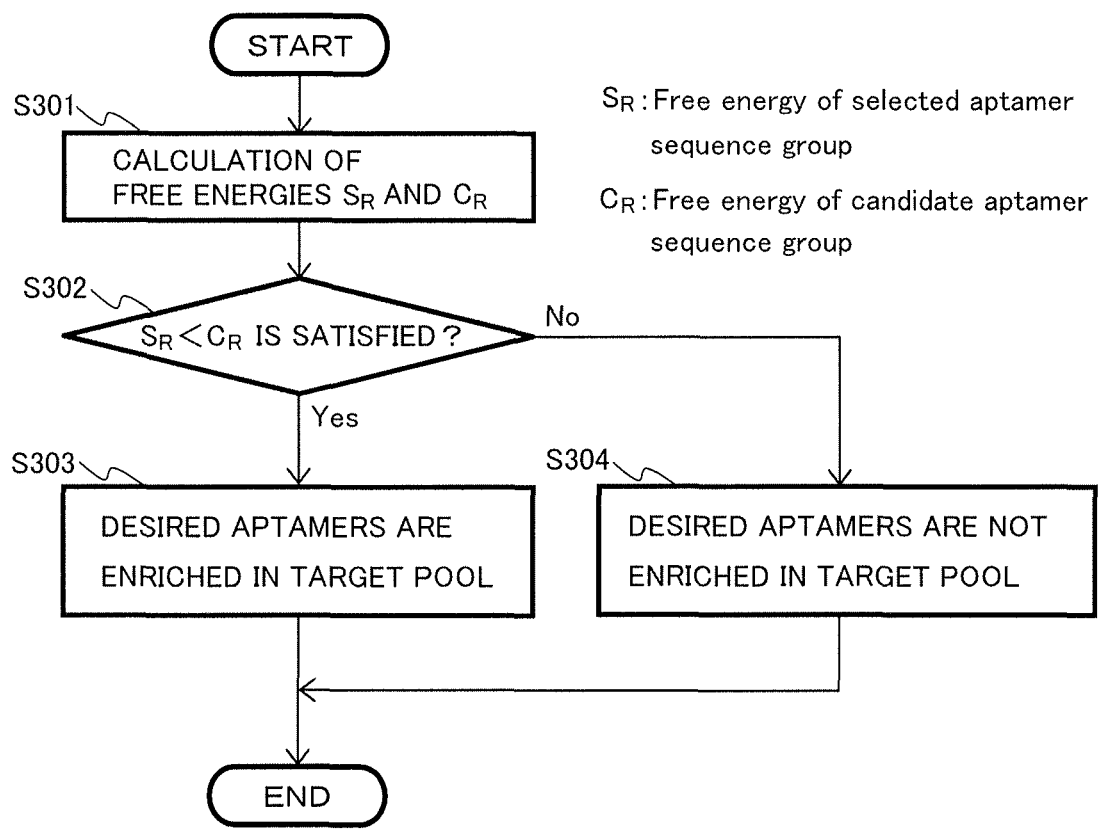
FIG. 3 is a flowchart illustrating the embodiment of the prediction method and prediction program according to the present invention.

Next, with reference to the flowcharts of FIGS. 2 and 3, a prediction method of the present embodiment will be described. The prediction method of the present embodiment includes a free energy calculation step (S21) and an enrichment prediction step (S22).

[Free Energy Calculation Step]

From the sequence information on the candidate aptamer sequence group in the reference pool and the sequence information on the selected aptamer sequence group in the target pool, the free energy ($C_R$) of the candidate aptamer sequence group and the free energy ($S_R$) of the selected aptamer sequence group are calculated, respectively (S301). The free energy calculation step can be carried out by the free energy calculation unit 12, for example. Hereinafter, "$C_R$" also is referred to as the free energy of the reference pool, and "$S_R$" also is referred to as the free energy of the target pool (the same applies hereinafter).

[Enrichment Prediction Step]

The free energy ($S_R$) of the selected aptamer sequence group in the target pool is compared with the free energy ($C_R$) of the candidate aptamer sequence group in the reference pool to determine whether or not the free energy ($S_R$) of the selected aptamer sequence group is lower than the free energy ($C_R$) of the candidate aptamer sequence group, i.e., whether or not "$S_R<C_R$" is satisfied (S302).

$S_R$: the free energy of the selected aptamer sequence group $C_R$: the free energy of the candidate aptamer sequence group Then, when the free energy ($S_R$) of the selected aptamer sequence group is lower than the free energy ($C_R$) of the candidate aptamer sequence group, it is predicted that the desired aptamers in the target pool are more enriched than those in the reference pool (S303). When the free energy ($S_R$) of the selected aptamer sequence group is the same as or higher than the free energy ($C_R$) of the candidate aptamer sequence group, it is predicted that the desired aptamers are not enriched in the target pool (S304). Through the above-described steps, the enrichment prediction is completed.

In the case where, for example, sequence information on aptamer sequence groups in pools of two or more rounds or all the rounds has been inputted as described above, the following steps may be performed repeatedly, for example: the step of selecting, from the aptamer sequence groups in the plurality of pools, aptamer sequence groups in any of the pools as the candidate aptamer sequence group in the reference pool and the selected aptamer sequence group in the target pool; the step of calculating the free energies of the thus-selected candidate aptamer sequence group and selected aptamer sequence group; and the step of predicting enrichment. Alternatively, for example, subsequent to the step of calculating the free energies of the respective aptamer sequence groups in the plurality of pools, the step of selecting aptamer sequence groups in any of the pools as the candidate aptamer sequence group in the reference pool and the selected aptamer sequence group in the target pool and the step of predicting enrichment may be performed repeatedly. In these cases, the same reference pool or different reference pools may be used in the respective enrichment prediction steps, for example. By doing so, it is possible to predict which of the plurality of pools is the one in which desired aptamer sequences are enriched.

The results of prediction may be outputted by the output unit 14 in accordance with the conditions specified by the user, for example. The output unit 14 may have a function of outputting the sequence information on the candidate aptamer sequence, the sequence information on the selected aptamer sequence, the free energies, etc., in addition to the results of prediction, for example.

Embodiment 2

Figure 4:
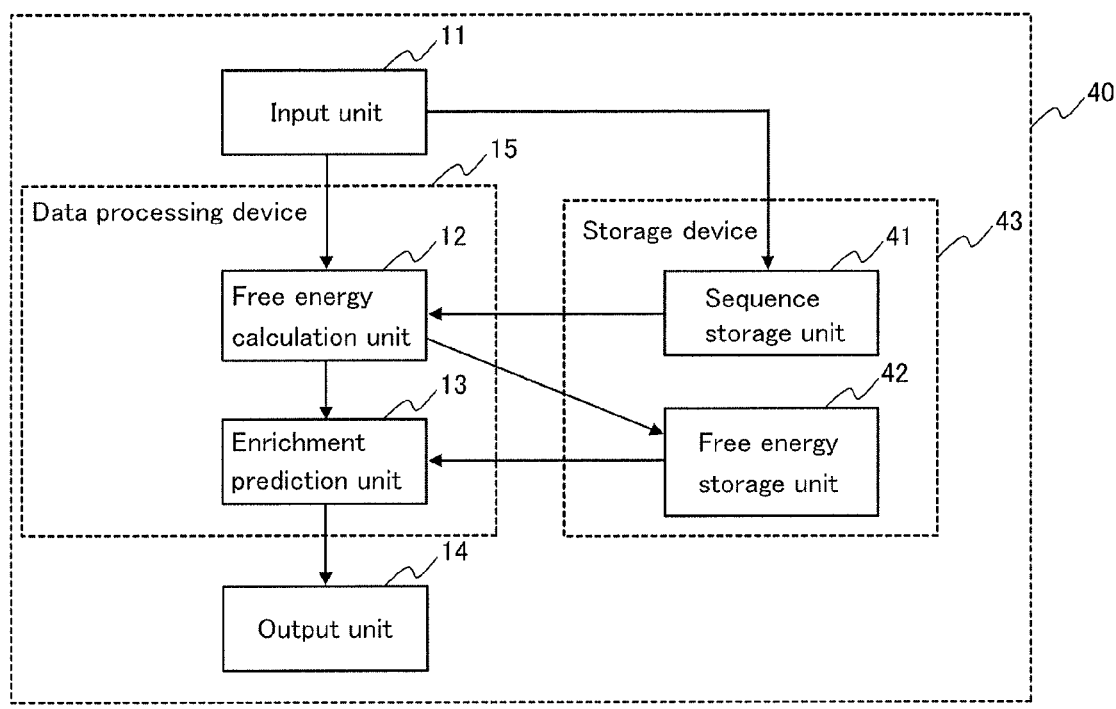
FIG. 4 is a block diagram showing another embodiment of the prediction device according to the present invention.

FIG. 4 shows an example of the configuration of a prediction device 40 according to the present embodiment. In FIG. 4, the same components as those in FIG. 1 are given the same reference numerals. Unless otherwise stated, the present embodiment is the same as Embodiment 1. As shown in FIG. 4, the prediction device 40 has the same configuration as the prediction device of Embodiment 1, except that it further includes a sequence storage unit 41 and a free energy storage unit 42. In other words, the prediction device 40 includes an input unit 11, a free energy calculation unit 12, an enrichment prediction unit 13, an output unit 14, the sequence storage unit 41, and the free energy storage unit 42. As shown in FIG. 4, the free energy calculation unit 12 and the enrichment prediction unit 13 may be incorporated in a data processing device 15, which is hardware, for example. The free energy calculation unit 12 and the enrichment prediction unit 13 each may be software itself, or may be hardware with installed software, for example. The data processing device 15 may include CPU and the like, for example. As shown in FIG. 4, the sequence storage unit 41 and the free energy storage unit 42 may be incorporated in a storage device 43, which is hardware, for example.

As shown in FIG. 4, the sequence storage unit 41 is connected electrically to the input unit 11 and the free energy calculation unit 12, for example. The free energy storage unit 42 is connected electrically to the free energy calculation unit 12 and the enrichment prediction unit 13, for example.

The sequence storage unit 41 stores information on the aptamer sequences inputted through the input unit 11, and outputs the information to the free energy calculation unit 12, for example.

The free energy storage unit 42 stores the free energies calculated by the free energy calculation unit 12 in association with the corresponding pools, i.e., the reference pool and the target pool, and outputs information on the free energies to the enrichment prediction unit 13.

In the case where sequence information on aptamer sequence groups in pools of a plurality of rounds has been inputted through the input unit 11 as described above, the sequence storage unit 41 may store the sequence information on the aptamer sequences in the pools of all the rounds or two or more rounds, for example, and output the information to the free energy calculation unit 12. Then, the free energy storage unit 42 may store the free energies calculated by the free energy calculation unit 12 in association with the corresponding pools. Among these free energies, the free energy storage unit 42 may output the information on the free energies of any two pools selected as the reference pool and the target pool to the enrichment prediction unit 13.

Embodiment 3

The present embodiment is an example where the virtual aptamer sequence group (2) is used as the reference aptamer sequence group. The virtual aptamer sequence group (2) is a virtual aptamer sequence group that is derived from the target aptamer sequence group and includes virtual aptamer sequences having the same base composition as the target aptamer sequence group.

Hereinafter, in the present embodiment, the reference aptamer sequences also are referred to as the "virtual aptamer sequences", the reference aptamer sequence group also is referred to as the "virtual aptamer sequence group", and the target aptamer sequence group including selected aptamer sequences also is referred to as the "selected aptamer sequence group".

Figure 5A:
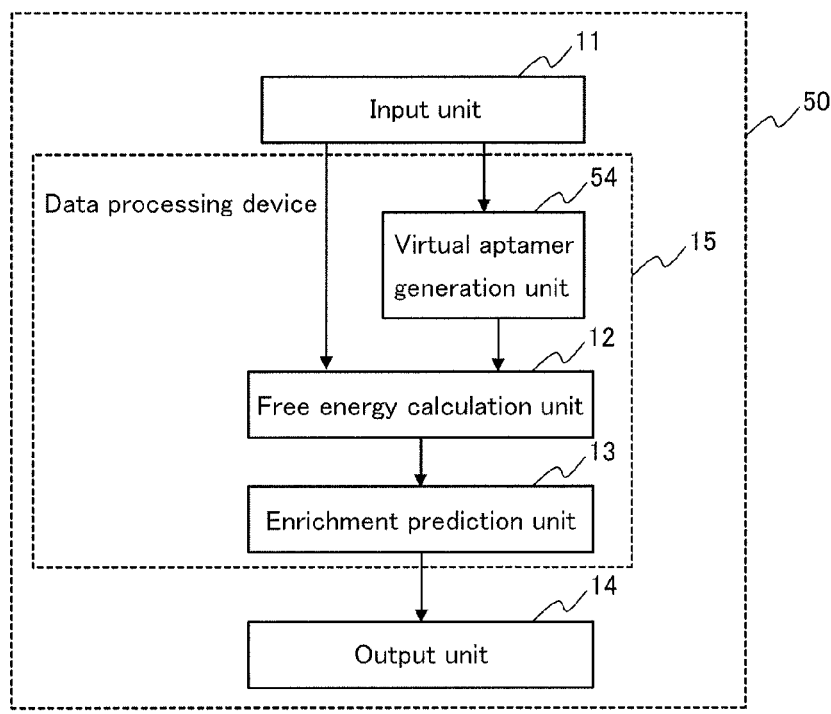
FIG. 5 is a block diagram showing still another embodiment of the prediction device according to the present invention.

FIG. 5A shows an example of the configuration of the prediction device of the present embodiment. In FIG. 5A, the same components as those in FIG. 1A are given the same reference numerals. Unless otherwise stated, the present embodiment is the same as Embodiment 1.

Figure 5B:
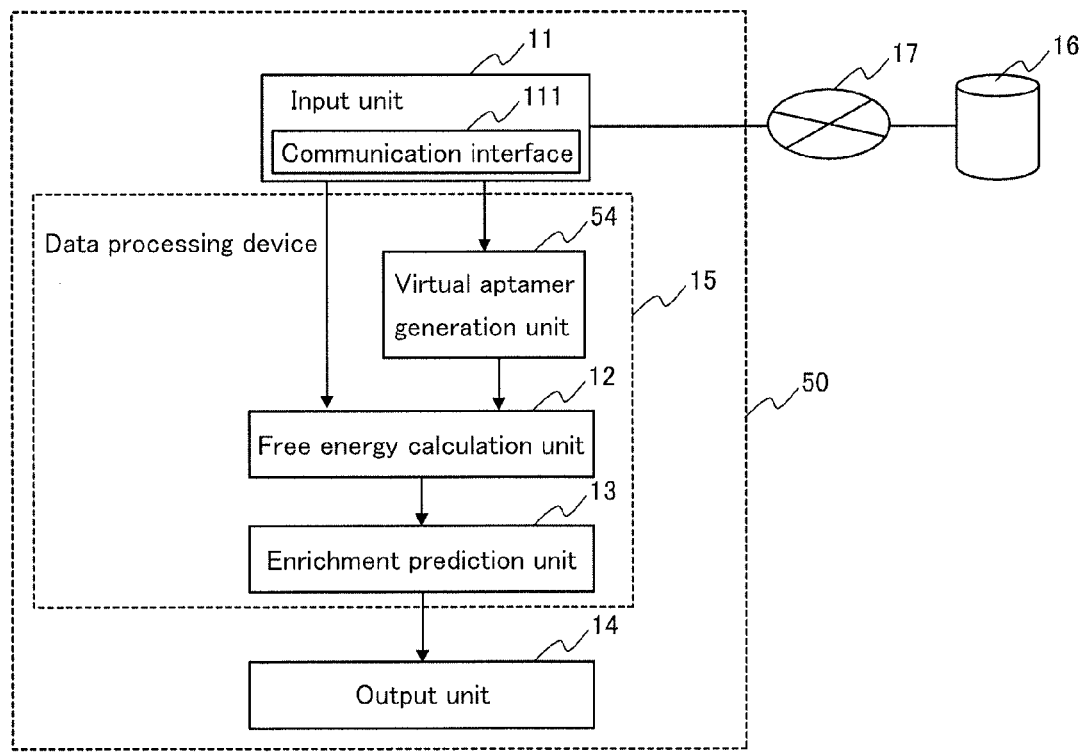

As shown in FIG. 5A, a prediction device 50 has the same configuration as the prediction device 10 of Embodiment 1 shown in FIG. 1A, except that it further includes a virtual aptamer generation unit 54. Specifically, the prediction device 50 includes an input unit 11, the virtual aptamer generation unit 54, a free energy calculation unit 12, an enrichment prediction unit 13, and an output unit 14. As shown in FIG. 5A, the virtual aptamer generation unit 54, the free energy calculation unit 12, and the enrichment prediction unit 13 may be incorporated in a data processing device 15, which is hardware, for example. The virtual aptamer generation unit 54, the free energy calculation unit 12, and the enrichment prediction unit 13 each may be software itself, or may be hardware with installed software, for example. As shown in FIG. 5B, the input unit 11 may be a unit for reading out sequence information on the candidate aptamer sequence group and the selected aptamer sequence group, which is stored in a database, for example. In this case, for example, as shown in FIG. 5B, the sequence information previously stored in a server 16 is read out by the input unit 11 through a line network 17. The input unit 11 may include, for example, a communication interface 111, as shown in FIG. 5B. In FIG. 5B, the same components as those in FIG. 5A are given the same reference numerals.

As shown in FIG. 5A, the virtual aptamer generation unit 54 is connected electrically to the input unit 11 and the free energy calculation unit 12, for example.

Based on the inputted sequence information on the selected aptamer sequence group in the target pool, the virtual aptamer generation unit 54 generates virtual aptamer sequences having the same base composition as the selected aptamer sequence group, thus generating a virtual aptamer sequence group including the virtual aptamer sequences. The virtual aptamer sequences can be generated based on the base composition in the selected aptamer sequence group in the target pool, for example. Specifically, for example, based on information on the base sequences of the respective selected aptamer sequences included in the selected aptamer sequence group, the appearance frequency of each base in the selected aptamer sequence group is determined, and is set as the base composition. Then, base sequences that can have this base composition are generated randomly, thereby providing a plurality of virtual aptamer sequences having the same base composition. Thus, the virtual aptamer sequence group including the virtual aptamer sequences can be obtained. In the present embodiment, as the sequence information on the selected aptamer sequence group in the target pool, the base composition thereof may be inputted through the input unit 11, for example. In this case, virtual aptamer sequences can be generated based on the inputted base composition, for example. The number of virtual aptamers to be generated is not particularly limited, and is, for example, 100 to 10,000,000, preferably 1,000 to 1,000,000, and more preferably 10,000 to 100,000. The sequence information on the virtual aptamer sequence group may be inputted through the input unit 11, for example.

Based on the inputted sequence information on the virtual aptamer sequence group derived from the target aptamer sequence group, the free energy calculation unit 12 calculates the free energy of the virtual aptamer sequence group. The free energy can be calculated in the above-described manner, for example.

The enrichment prediction unit 13 retrieves the free energy information from the free energy calculation unit 12, and compares the free energy of the selected aptamer sequence group with the free energy of the virtual aptamer sequence group derived from the selected aptamer sequence group. Then, when the free energy of the selected aptamer sequence group is lower than the free energy of the virtual aptamer sequence group, the enrichment prediction unit 13 predicts that the desired aptamer sequences are enriched in the target pool.

It is preferable to predict that the desired aptamer sequences are enriched in the target pool when, for example, the free energy of the selected aptamer sequence group is significantly lower than the free energy of the virtual aptamer sequence group derived from the selected aptamer sequence group, because this improves the reliability of the results of prediction. The method for determining whether or not the difference between these free energies is significant is not particularly limited, and may be the same as described above.

In the present embodiment, for example, the free energy of the selected aptamer sequence group in the target pool also may be compared with the free energy of the candidate aptamer sequence group in the reference pool, as in Embodiment 1.

Similarly to the prediction device 40 of Embodiment 2 shown in FIG. 4, the prediction device of the present embodiment also may further include a sequence storage unit 41 and a free energy storage unit 42, for example. The sequence storage unit 41 may store, in addition to the sequence information on the selected aptamer sequence group in the target pool, sequence information on the virtual aptamer sequence group generated by the virtual aptamer generation unit, and may output the information to the free energy calculation unit 12, for example. The sequence storage unit 41 further may store sequence information on the candidate aptamer sequence group in the reference pool, and may output the sequence information to the free energy calculation unit 12. The free energy storage unit 42 may store, in addition to the free energy of the selected aptamer sequence group in the target pool calculated by the free energy calculation unit 12, the free energy of the virtual aptamer sequence group derived from the selected aptamer sequence group in association with the target pool, and may output the free energy information to the enrichment prediction unit 13, for example. Also, the free energy storage unit 42 further may store the free energy of the candidate aptamer sequence group in the reference pool in association with the reference pool, and may output the free energy information to the enrichment prediction unit 13.

Figure 6:
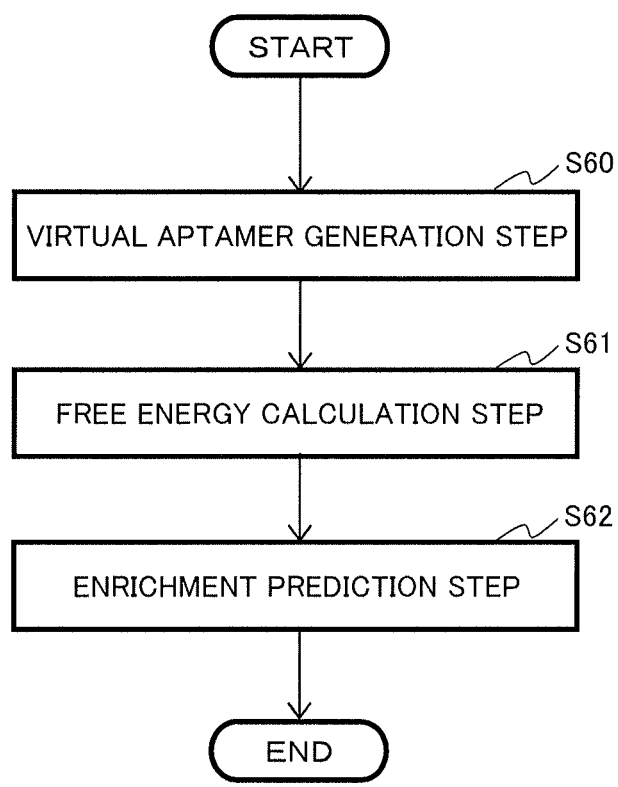
FIG. 6 is a flowchart illustrating another embodiment of the prediction method and prediction program according to the present invention.
Figure 7:
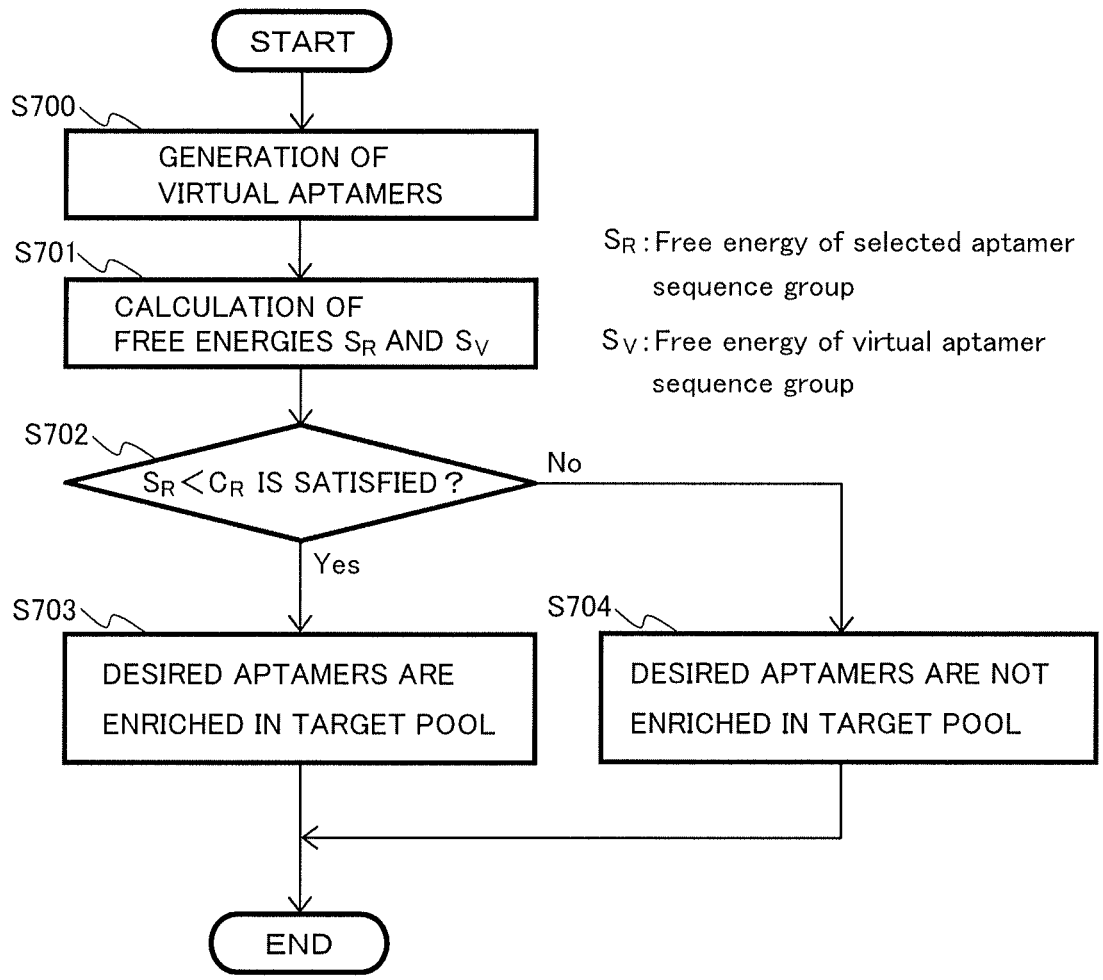
FIG. 7 is a flowchart illustrating the embodiment of the prediction method and prediction program according to the present invention.

Next, with reference to the flowcharts of FIGS. 6 and 7, a prediction method of the present embodiment will be described. The prediction method of the present embodiment includes a virtual aptamer generation step (S60), a free energy calculation step (S61), and an enrichment prediction step (S62).

[Virtual Aptamer Generation Step]

Based on the selected aptamer sequence group in the target pool, the virtual aptamer sequence group including the virtual aptamer sequences having the same base composition as the target aptamer sequence group is generated (S700).

[Free Energy Calculation Step]

Subsequently, from the sequence information on the selected aptamer sequence group in the target pool and the sequence information on the virtual aptamer sequence group derived from the selected aptamer sequence group, the free energy ($S_R$) of the selected aptamer sequence group and the free energy ($S_V$) of the virtual aptamer sequence group are calculated, respectively (S701). This free energy calculation step can be carried out by the free energy calculation unit 12, for example. Hereinafter, "$S_R$" also is referred to as the free energy of the target pool, and "$S_V$" also is referred to as the free energy of the reference pool (the same applies hereinafter).

[Enrichment Prediction Step]

The calculated free energy ($S_R$) of the selected aptamer sequence group in the target pool is compared with the calculated free energy ($S_V$) of the virtual aptamer sequence group derived from the selected aptamer sequence group to determine whether or not the free energy ($S_R$) of the selected aptamer sequence group is lower than the free energy ($S_V$) of the virtual aptamer sequence group, i.e., whether or not "$S_R<S_V$" is satisfied (S702).

$S_R$: the free energy of the selected aptamer sequence group $S_V$: the free energy of the virtual aptamer sequence group Then, when the free energy ($S_R$) of the selected aptamer sequence group in the target pool is lower than the free energy ($S_V$) of the virtual aptamer sequence group derived from the selected aptamer sequence group, it is predicted that the desired aptamers are enriched in the target pool (S703). When the free energy ($S_R$) of the selected aptamer sequence group in the target pool is the same as or higher than the free energy ($S_V$) of the virtual aptamer sequence group derived from the selected aptamer sequence group, it is predicted that the desired aptamers are not enriched in the target pool (S704). Through the above-described steps, the enrichment prediction is completed.

In the present embodiment, for example, the prediction of enrichment is possible merely by comparing the free energy of the selected aptamer sequence group in the target pool with the free energy of the virtual aptamer sequence group derived from the selected aptamer sequence group.

In the present embodiment, for example, in the free energy calculation step, the free energy ($C_R$) of the candidate aptamer sequence group in the reference pool also may be calculated, as in Embodiment 1. Then, in the enrichment prediction step, it is also possible to predict enrichment by comparing the free energy ($S_R$) of the selected aptamer sequence group in the target pool with the free energy ($C_R$) of the candidate aptamer sequence group in the reference pool.

Embodiment 4

The present embodiment is directed to an example where the candidate aptamer sequence group (1), the virtual aptamer sequence group (2), and the virtual aptamer sequence group (3) are used as the reference aptamer sequence groups. Unless otherwise stated, Embodiment 4 can be carried out in the same manner as Embodiment 1, Embodiment 2 and Embodiment 3.

(1) the candidate aptamer sequence group including a plurality of candidate aptamer sequences
(2) the virtual aptamer sequence group that is derived from the target aptamer sequence group and includes virtual aptamer sequences having the same base composition as the target aptamer sequence group
(3) the virtual aptamer sequence group that is derived from the candidate aptamer sequence group and includes virtual aptamer sequences having the same base composition as the candidate aptamer sequence group The prediction method of the present embodiment includes a virtual aptamer generation step, a free energy calculation step, and an enrichment prediction step.

[Virtual Aptamer Generation Step]

Based on the selected aptamer sequence group in the target pool, the virtual aptamer sequence group that is derived from the selected aptamer sequence group and includes virtual aptamer sequences having the same base composition as the selected aptamer sequence group (2) is generated. On the other hand, based on the candidate aptamer sequence group in the reference pool (1), the virtual aptamer sequence group that is derived from the candidate aptamer sequence group and includes virtual aptamer sequences having the same base composition as the candidate aptamer sequence group (3) is generated.

[Free Energy Calculation Step]

Subsequently, from the selected aptamer sequence group in the target pool and the virtual aptamer sequence group derived from the selected aptamer sequence group (2), the free energy ($S_R$) of the selected aptamer sequence group and the free energy ($S_V$) of the virtual aptamer sequence group derived from the selected aptamer sequence group (2) are calculated, respectively. On the other hand, from the candidate aptamer sequence group in the reference pool (1) and the virtual aptamer sequence group derived from candidate aptamer sequence group (3), the free energy ($C_R$) of the candidate aptamer sequence group (1) and the free energy ($C_V$) of the virtual aptamer sequence group derived from candidate aptamer sequence group (3) are calculated, respectively. The step of calculating these free energies can be carried out by the free energy calculation unit 12, for example.

[Enrichment Prediction Step]

The free energy ($S_R$) of the selected aptamer sequence group in the target pool is compared with the free energy ($S_V$) of the virtual aptamer sequence group derived from the selected aptamer sequence group (2) to determine whether or not the free energy ($S_R$) of the selected aptamer sequence group is lower than the free energy ($S_V$) of the virtual aptamer sequence group (2), i.e., whether or not "$S_R<S_V$" is satisfied.

$S_R$: the free energy of the selected aptamer sequence group $S_V$: the free energy of the virtual aptamer sequence group On the other hand, the calculated free energy ($C_R$) of the candidate aptamer sequence group in the reference pool (1) is compared with the free energy ($C_V$) of the virtual aptamer sequence group derived from the candidate aptamer sequence group (3) to determine whether or not the free energy ($C_R$) of the candidate aptamer sequence group (1) is lower than the free energy ($C_V$) of the virtual aptamer sequence group (3), i.e., whether or not "$C_R<C_V$" is satisfied.

$C_R$: the free energy of the candidate aptamer sequence group $C_V$: the free energy of the virtual aptamer sequence group Next, regarding the target pool, the reduction of the free energy ($S_R$) of the selected aptamer sequence group relative to the free energy ($S_V$) of the virtual aptamer sequence group derived from the selected aptamer sequence group (2) is determined ($S_V$–$S_R$). Also, regarding the reference pool, the reduction of the free energy ($C_R$) of the candidate aptamer sequence group (1) relative to the free energy ($C_V$) of the virtual aptamer sequence group derived from the candidate aptamer sequence group (3) is determined ($C_V$–$C_R$). Then, when the reduction in the target pool ($S_V$–$S_R$) is greater than the reduction in the reference pool ($C_V$–$C_R$), it can be predicted that the desired aptamer sequences in the target pool are more enriched than those in the reference pool.

Embodiment 5

In the case where, regarding the target pool, the free energy of the selected aptamer sequence group is compared with the free energy of the virtual aptamer sequence group derived from the selected aptamer sequence group (2), whether the difference between these free energies is significant can be determined by the following methods, for example. It is to be noted, however, that these methods merely are illustrative examples and do not limit the present invention by any means. The same apples to the case where, regarding the reference pool, the free energy of the candidate aptamer sequence group (1) is compared with the free energy of the virtual aptamer sequence group derived from the candidate aptamer sequence group (3).

(1) Comparison Between Two Groups

On the basis of the frequency of each base (A, G, C, and T and/or U) in a selected aptamer sequence group S contained in the target pool, random sequences that exhibit the same frequency are generated, thus providing a virtual aptamer sequence group $S_r$. The free energies calculated from the selected aptamer sequence group S are represented by "g", and the free energies calculated from the virtual aptamer sequence group $S_r$ are represented by "$g_r$". In a pool in which desired aptamer sequences are enriched, the free energy distribution in a selected aptamer sequence group is significantly lower than the free energy distribution in a virtual aptamer sequence group, as described above. Therefore, when the distribution of the free energies g in the selected aptamer sequence group is lower than the distribution of the free energies $g_r$ in the virtual aptamer sequence group, it can be said that the desired aptamer sequences are enriched in the pool. In order to demonstrate that the distribution of the free energies g in the selected aptamer sequence group is lower than the distribution of the free energies $g_r$ in the virtual aptamer sequence group, a hypothesis represented by the following expressions (1) is formulated. In the following expressions, $\mu$ is the mean of the free energies g in the selected aptamer sequence group, and $\mu_r$ is the mean of the free energies $g_r$ in the virtual aptamer sequence group. When this hypothesis is refuted, it is demonstrated that the mean of the free energies g in the selected aptamer sequence group is significantly lower than the mean of the free energies $g_r$ in the virtual aptamer sequence group.

$$H_{Null}: \mu \geq \mu_r, H_{Alt}: \mu < \mu_r \tag{1}$$

In this example, the difference between these mean values is examined by the Welch's t test. The t value is represented by the following expression (2), and follows the t distribution with the degree of freedom v. n is the number of the selected aptamer sequences in the selected aptamer sequence group S, and $n_r$ is the number of virtual aptamer sequences in the virtual aptamer sequence group. v is represented by the following expression (3) where an estimate of the variance is used.

$$t = \frac{\hat{\mu} - \hat{\mu}_r}{\sqrt{\frac{\hat{\sigma}^2}{n} + \frac{\hat{\sigma}_r^2}{n_r}}} \sim t(v) \tag{2}$$

$$v = \frac{\left(\frac{\hat{\sigma}^2}{n} + \frac{\hat{\sigma}_r^2}{n}\right)^2}{\frac{\hat{\sigma}^4}{n(n-1)} + \frac{\hat{\sigma}_r^4}{n_r(n_r-1)}} \tag{3}$$

(2) Comparison with Statistical Population

As in the above item (1), the free energies calculated from the selected aptamer sequence group S contained in the target pool are represented by g. Assuming that g follows the normal distribution, the following expression (4) is obtained.

$$G \sim N(\mu, \sigma^2) \tag{4}$$

Next, as in the above item (1), on the basis of the frequency of each base in the selected aptamer sequence group S, random sequences that exhibit the same frequency are generated, thus providing a virtual aptamer sequence group $S_r$. The free energies calculated from the virtual aptamer sequence group $S_r$ are represented by $g_r$, and the mean thereof is represented by $\mu_0$. A hypothesis represented by the following expression (5) is formulated. At this time, the t value is represented by the following expression (6) and follows the t distribution with the degree of freedom n−1. When this hypothesis is refuted, it is demonstrated that the mean $\mu$ of the free energies g in the selected aptamer sequence group is significantly lower than the mean $\mu_0$ of the free energies $g_r$ in the virtual aptamer sequence group.

$$H_{Null}: \mu \geq \mu_0, H_{Alt}: \mu < \mu_0 \tag{5}$$

$$t = \frac{\sqrt{n}(\hat{\mu} - \mu_0)}{\hat{\sigma}} \sim t(n-1) \tag{6}$$

(3) Parallel Shift of Distribution

When the free energy of the selected aptamer sequence group contained in the target pool is significantly lower than the free energy of the virtual aptamer sequence group derived from the selected aptamer sequence group, it is possible to determine whether the difference between these free energies is sufficient in the following manner, for example.

A hypothesis represented by the following expressions (7) is formulated. In the following expressions, $\mu$ is the mean of the free energies g calculated from the selected aptamer sequence group S, $\mu_0$ is the mean of the free energies $g_r$ calculated from the virtual aptamer sequence group $S_r$, and $\delta$ is a parameter indicating the difference between these means. At this time, the t value is represented by the following expression (8) and follows the t distribution with the degree of freedom n−1. When this hypothesis is refuted, it is demonstrated that the mean $\mu$ of the free energies g in the selected aptamer sequence group is significantly lower than the mean $\mu_0$ of the free energies $g_r$ in the virtual aptamer sequence group.

$$H_{Null}: \mu \geq \mu_0 - \delta, H_{Alt}: \mu < \mu_0 - \delta \tag{7}$$

$$t = \frac{\sqrt{n}(\hat{\mu} - (\mu_0 - \delta))}{\hat{\sigma}} \sim t(n-1) \tag{8}$$

Embodiment 6

When the free energy of the selected aptamer sequence group in the target pool is compared with the free energy of the candidate aptamer sequence group in the reference pool, it is possible to determine whether the difference between these free energies is significant in the following manner, for example.

(1) Comparison Between Rounds

The pool of the i-th round (i-th) is set as a reference pool. The distributions of free energies calculated from a candidate aptamer sequence group $S^i$ contained in the reference pool is represented by $\mu^i$. On the other hand, a pool of the j-th round (j-th), which is an arbitrary round subsequent to the i-th round, is set as a target pool. A selected aptamer sequence group contained in the target pool is represented by $S^j$, and the distribution of the free energies calculated from the selected aptamer sequence group $S^j$ is represented by $\mu^j$. It is to be noted that j>i. A hypothesis represented by the following expression (9) is formulated, and the Welch's t test is conducted. If the test result shows the difference is significant, the mean of the distributions $\mu^j$ of the free energies in the j-th round is lower than the mean of the distributions $\mu^i$ of the free energies in the i-th round. That is, it is possible to determine enrichment of desired aptamer sequences is more advanced in the j-th round than in the i-th round.

$$H_{Null}: \mu^j \geq \mu^i, H_{Alt}: \mu^j < \mu^i \quad (9)$$

The program of the present invention is a program that causes the above-described prediction device of the present invention to execute a method for using the prediction device. The program of the present invention may be recorded on a recording medium, for example. The recording medium is not particularly limited, and examples thereof include HDD, CD-ROM (CD-R, CD-RW), DVD, and a memory card. The program of the present invention may be installed previously in the above-described prediction device of the present invention, or may be installed in the same via the recording medium or a line network such as the Internet, for example. It is not always necessarily that the program of the present invention is installed in the above-described prediction device of the present invention. For example, the program of the present invention stored in a server may cause the above-described device to execute the above-described use method.

EXAMPLES

Hereinafter, the present invention will be described by way of examples. It is to be noted, however, that the present invention is by no means limited by the following examples.

Example 1

In the present example, using an initial pool containing a plurality of aptamers, desired primers that can bind to human HMGB1 (High Mobility Group Box 1; trade name "H4652 HMG-1", Sigma Chemical Co.) were enriched by the SELEX method.

A pool containing a plurality of aptamers was used as the initial pool of the round 0. The aptamers in the initial pool each had a primer region in its 3' end region and 5' end region and had a random region between the 3' end region and 5' end region. In these aptamers, the sequences of the primer regions were totally identical, and the sequences of the random regions were different from one another.

In the SELEX method, with selection and amplification of aptamers bound to the target as one set of processes to be performed in each round, the initial pool (R0) was subjected to the set of processes 8 times in total, and pools were obtained from the respective rounds (R1 to R8). The pools of the respective rounds were subjected to surface plasmon resonance analysis of intermolecular interaction using Biacore X (trade name, GE Healthcare UK Ltd.) to measure the binding ability to HMGB1 (Rmax: unit "RU").

Table 1 below shows information on the pool of each round. In Table 1, "Number" indicates the number of all the aptamers (the number of sequences) contained in the pool of each round; "Base composition" indicates, regarding the pool of each round, the base composition (the appearance frequency of each base) in the random region of all the aptamers contained in the pool; "Rmax" indicates the HMGB1-binding ability of the pool of each round; and "MFE mean" and "MFE variance" indicate the mean (kcal/mol) and variance ((kcal/mol)$^2$) of minimum free energies (MFE) in the pool of each round.

TABLE 1

| Round | Number | Base composition | | | | MFE mean (Kcal/mol) | MFE variance | Rmax (RU) |
|---|---|---|---|---|---|---|---|---|
| | | A | C | G | T | | | |
| R1 | 10635 | 0.2028 | 0.3078 | 0.1899 | 0.2994 | −18.68 | 15.34 | 44.90 |
| R2 | 10153 | 0.1945 | 0.3198 | 0.1826 | 0.3031 | −18.11 | 13.38 | 45.65 |
| R3 | 8122 | 0.1968 | 0.3203 | 0.1742 | 0.3087 | −17.69 | 13.51 | 41.30 |
| R4 | 9552 | 0.1999 | 0.3114 | 0.1709 | 0.3177 | −17.8 | 14.26 | 30.56 |
| R5 | 8232 | 0.196 | 0.318 | 0.1776 | 0.3082 | −18.65 | 18.12 | 11.81 |
| R6 | 2884 | 0.1948 | 0.3301 | 0.21 | 0.265 | −22.88 | 17.39 | 24.48 |
| R7 | 8785 | 0.1969 | 0.3192 | 0.2132 | 0.2707 | −23.45 | 12.33 | 85.44 |
| R8 | 9951 | 0.1947 | 0.3061 | 0.2313 | 0.2679 | −24.55 | 5.69 | 127.86 |

Furthermore, in order to verify the reliability of the analysis based on the free energies to be described below, surface plasmon resonance analysis of intermolecular interaction actually was performed with respect to the pools of the respective rounds to examine in which round the enrichment of the desired aptamers bound to HMGB1 was achieved. Specifically, regarding the pool of each round, the presence or absence of a duplicate sequence (the sequence of a plurality of the same aptamers significantly present in the pool) and the binding to HMGB1 was examined. Furthermore, by surface plasmon resonance analysis of intermolecular interaction, aptamers actually bound to HMGB1 (HMGB1-binding aptamers) were selected from the pool of R8, and the base sequence of the HMGB1-binding aptamers was determined. Still further, based on the sequences of the HMGB1-binding aptamers, motif analysis was conducted with respect to the aptamers contained in each pool.

As a result, in the pools of R1 to R3, no significantly present duplicate sequence was observed. In the pool of R4, although duplicate sequences having the motif of the HMGB1-binding aptamer sequence were detected, binding to HMGB1 did not occur, so that the HMGB1-binding aptamer sequences were not enriched. In the pool of R5, some kinds of duplicate sequences were detected actually, and it was found that the duplicate sequences with low appearance frequencies in the pool were the sequences of the aptamers bound to HMGB1. From this fact, it was found that the HMGB1-binding aptamers were enriched in the pool of R5. Also, in the pools of R6 and R7, some kinds of duplicate sequences were detected, and it was found that the duplicate sequences with high appearance frequencies (excluding the duplicate sequence with the highest appearance frequency) in the pool were the sequences of the aptamers bound to HMGB1. From this fact, it was found that the HMGB1-binding aptamers in the pools of R6 and 7 were more enriched than those in the pool of R5. Also, in the pool of R8, some kinds of duplicate sequences were detected, and it was found that some kinds of duplicate sequences with high appearance frequencies including the highest appearance frequency in the pool were the sequences of the aptamers bound to HMGB1. Since the duplicate sequences with high appearance frequencies including the highest appearance frequency bound to HMGB1, it was found that the HMGB1-binding aptamers in the pool of R8 were still more enriched than those in the pools of R6 and R7. From these results, in the analysis based on the free energies to be described below, if the difference in free energy was found to be significant in the pools of R1 to R4, the analysis result was considered to be false positive, and if the difference in free energy was not found to be significant in the pools of R5 to R8, the analysis result was considered to be false negative.

(1-1) Free Energy of Virtual Aptamer Sequences

Based on the base composition in each round shown in Table 1, virtual aptamer sequences having the same base composition were generated on a computer. The number of virtual aptamer sequences was set to 1,000, 10,000, and 100,000. Then, the free energies of the respective virtual aptamer sequences were determined, and the mean and variance of the free energies in the pool of each round were calculated. The generation of the virtual aptamer sequences and the calculation of the mean and variance of the free energies were carried out 10 times in total (n=10).

Figure 8A:
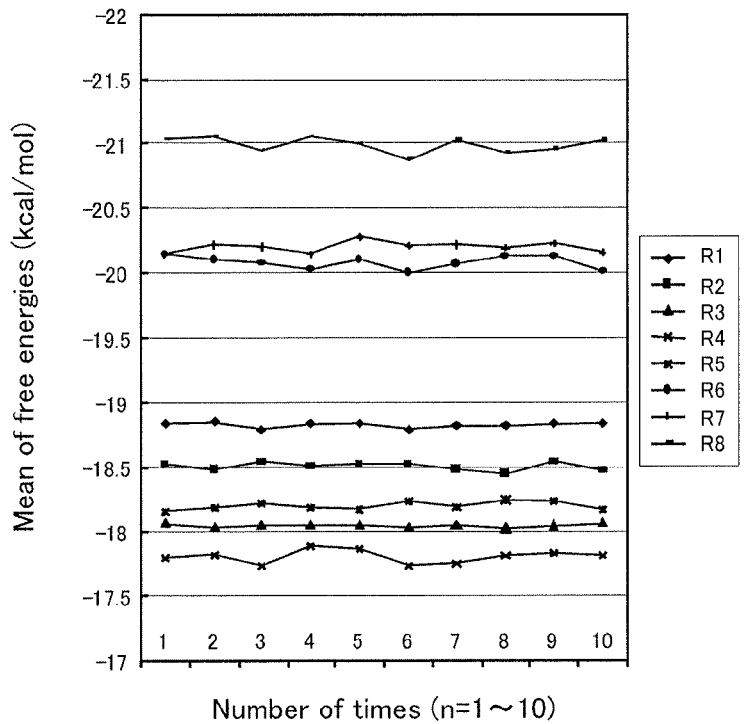
FIG. 8A is a graph showing the mean of free energies in a virtual aptamer sequence group including 10,000 virtual aptamer sequences in Example 1 of the present invention.
Figure 8B:
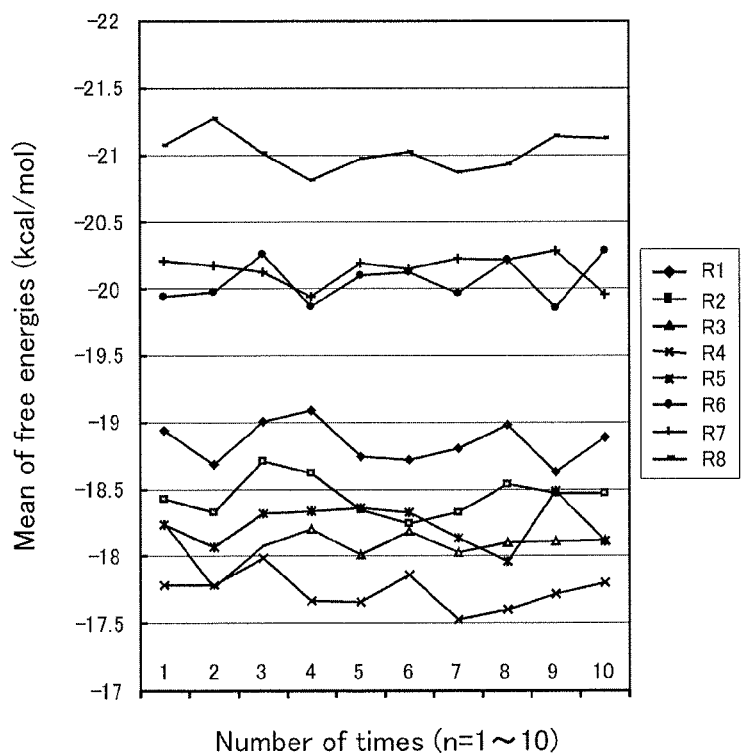
FIG. 8B is a graph showing the mean of free energies in a virtual aptamer sequence group including 1,000 virtual aptamer sequences in Example 1 of the present invention.

FIG. 8 shows the mean of the free energies in each round, obtained in the 10 trials. FIG. 8A shows the results obtained when 10,000 virtual aptamer sequences were generated per round, and FIG. 8B shows the results obtained when 1,000 virtual aptamer sequences were generated per round. In FIG. 8, the vertical axis indicates the mean of the free energies (unit: kcal/mol), and the horizontal axis indicates the number of trials (n=1 to 10). As shown in FIG. 8, in the case where 1,000 or 10,000 virtual aptamer sequences were generated in each round, the mean of the free energies was substantially constant throughout the 10 trials. In particular, it was found that, by generating 10,000 virtual aptamer sequences, the mean of the free energies can be calculated very stably.

Figure 9:
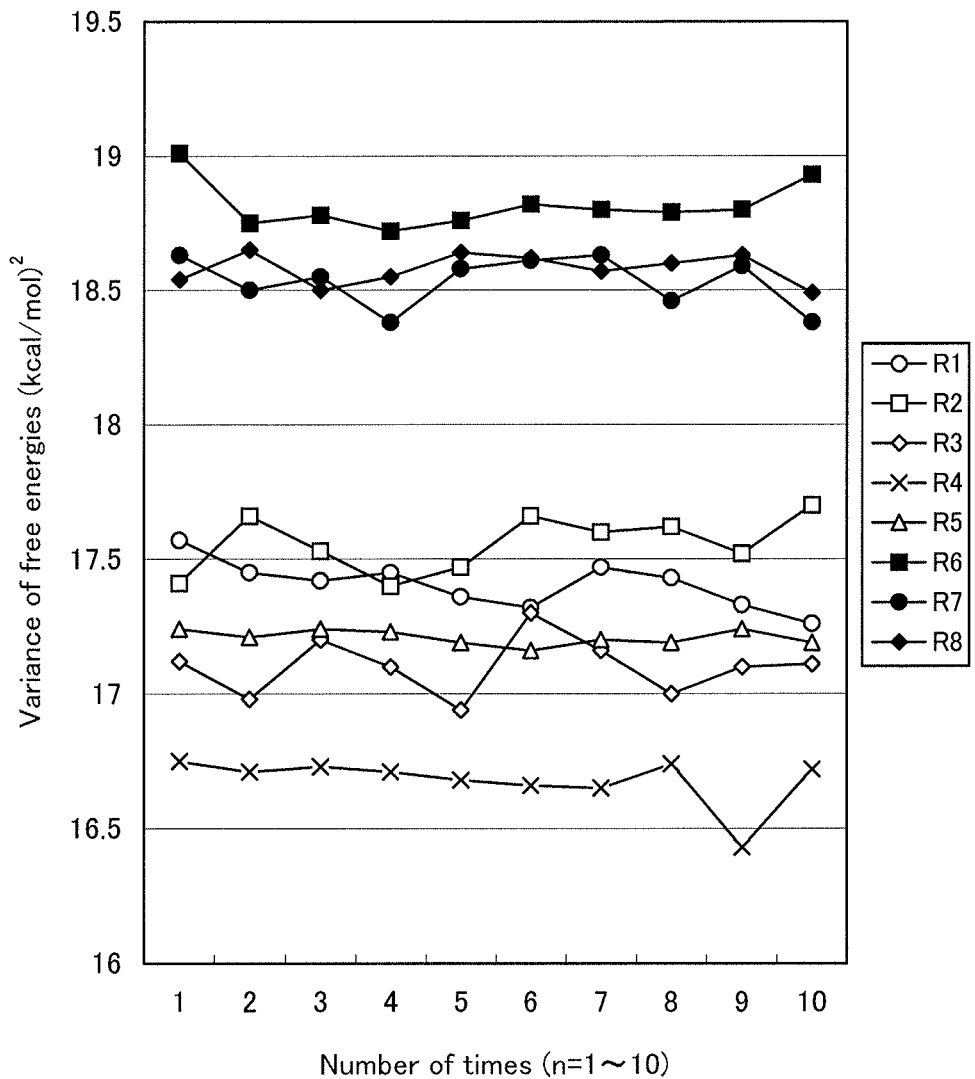
FIG. 9 is a graph showing the variance of free energies in a virtual aptamer sequence group including 100,000 virtual aptamer sequences in Example 1 of the present invention.

FIG. 9 shows the variance of the free energies in each round, obtained in the 10 trials. FIG. 9 shows the results obtained when 100,000 virtual aptamer sequences were generated per round. In FIG. 9, the vertical axis indicates the variance of the free energies (unit: (kcal/mol)$^2$), and the horizontal axis indicates the number of trials (n=1 to 10). As shown in FIG. 9, in the case where 100,000 virtual aptamer sequences were generated in each round, the free energy of the virtual aptamer sequences was substantially constant throughout the 10 trials.

(1-2) Comparison Between Sampled Aptamer Sequences and Virtual Aptamer Sequences From the pools of the respective rounds shown in Table 1, a predetermined number of aptamer sequences were taken as samples. The number of the aptamer sequences taken as samples was set to 20, 40, 60, 80, 100, 120, 140, 160, 180, or 200. The base compositions in random regions of all the predetermined number of sampled aptamer sequences taken from the respective rounds were analyzed. Then, based on the thus-analyzed base compositions of the respective rounds, 10,000 virtual aptamer sequences having the same base compositions were generated on a computer. Subsequently, the free energies of the sampled aptamer sequences and the virtual aptamer sequences were determined using RNAfold (Andreas R Gruber et al., The vienna rna websuite. Nucleic Acids Res, 36 (Web Server issue): W70-W74, July 2008). Then, the mean of the free energies of the sampled aptamer sequences and the mean of the free energies of the virtual aptamer sequences in the pools of the respective rounds were calculated. The free energies were calculated under the following conditions: a temperature of 37° C., a minimum stem length of 2 base pairs (hereinafter the same). The generation of the virtual aptamer sequences and the calculation of the mean of the free energies were carried out 100 times in total (n=100). Then, among the 100 trials, the number of times the mean free energy ($S_R$) of the sampled aptamer sequences was lower than the mean free energy ($S_V$) of the virtual aptamer sequences was counted.

The results thereof are shown in Table 2 below. Table 2 shows, for each round and each number of samples, the number of times the mean free energy ($S_R$) of the sampled aptamer sequences was lower than the mean free energy ($S_V$) of the virtual aptamer sequences. Table 2 also shows the binding ability (Rmax) of the pool of each round.

TABLE 2

| Number of samples | Number of the times $S_R < S_V$ was satisfied (in 100 trials) | | | | | | | |
|---|---|---|---|---|---|---|---|---|
| | R1 | R2 | R3 | R4 | R5 | R6 | R7 | R8 |
| 20 | 36 | 20 | 21 | 54 | 73 | 100 | 100 | 100 |
| 40 | 35 | 8 | 22 | 48 | 85 | 100 | 100 | 100 |
| 60 | 36 | 15 | 10 | 47 | 89 | 100 | 100 | 100 |
| 80 | 31 | 6 | 11 | 57 | 92 | 100 | 100 | 100 |
| 100 | 26 | 8 | 18 | 55 | 92 | 100 | 100 | 100 |
| 120 | 33 | 4 | 7 | 48 | 97 | 100 | 100 | 100 |
| 140 | 28 | 5 | 5 | 50 | 98 | 100 | 100 | 100 |
| 160 | 26 | 4 | 3 | 58 | 98 | 100 | 100 | 100 |
| 180 | 24 | 2 | 1 | 57 | 99 | 100 | 100 | 100 |
| 200 | 15 | 1 | 4 | 52 | 98 | 100 | 100 | 100 |
| Rmax (RU) | 44.90 | 45.65 | 41.30 | 30.56 | 11.81 | 24.48 | 85.44 | 127.86 |

As a result of the free energy analysis, as can be seen from Table 2, regardless of the number of samples, the number of times $S_R<S_V$ was satisfied increased from R5 to be close to 100, and reached 100 in R6 and the rounds subsequent thereto. These results agreed with the results of the above-described surface plasmon resonance analysis of intermolecular interaction where the binding to HMGB1 was actually examined. Thus, it can be said that the free energy analysis can determine whether or not aptamer sequences that can bind to a target substance are enriched with high sensitivity.

Moreover, among the above-described 100 trials, the number of times the mean free energy ($S_R$) of the sampled aptamer sequences was lower than the mean free energy ($S_V$) of the virtual aptamer sequences was counted according to the t test with the significance level set at 5%.

The results thereof are shown in Table 3 below. Table 3 shows, for each round and each number of samples, the number of times the mean free energy ($S_R$) of the sampled aptamer sequences was lower than the mean free energy ($S_V$) of the virtual aptamer sequences with the significance level of 5%. Table 3 also shows the binding ability (Rmax) of the pool of each round.

TABLE 3

| Number of samples | Number of the times $S_R < S_v$ was satisfied (significance level: 5%) (in 100 trials) | | | | | | | |
|---|---|---|---|---|---|---|---|---|
| | R1 | R2 | R3 | R4 | R5 | R6 | R7 | R8 |
| 20 | 0 | 0 | 0 | 0 | 0 | 93 | 99 | 100 |
| 40 | 0 | 0 | 0 | 0 | 6 | 100 | 100 | 100 |
| 60 | 0 | 0 | 0 | 0 | 4 | 100 | 100 | 100 |
| 80 | 0 | 0 | 0 | 0 | 9 | 100 | 100 | 100 |
| 100 | 0 | 0 | 0 | 0 | 11 | 100 | 100 | 100 |
| 120 | 0 | 0 | 0 | 0 | 9 | 100 | 100 | 100 |
| 140 | 0 | 0 | 0 | 0 | 15 | 100 | 100 | 100 |
| 160 | 0 | 0 | 0 | 0 | 22 | 100 | 100 | 100 |
| 180 | 0 | 0 | 0 | 1 | 16 | 100 | 100 | 100 |
| 200 | 0 | 0 | 0 | 0 | 24 | 100 | 100 | 100 |
| Rmax (RU) | 44.90 | 45.65 | 41.30 | 30.56 | 11.81 | 24.48 | 85.44 | 127.86 |

As a result, as can be seen from Table 3, regardless of the number of samples, the number of times $S_R < S_V$ was satisfied (significance level: 5%) was substantially 0 until R4. It increased from R5, and reached 100 in R6 and the rounds subsequent thereto. When the number of samples was 40 or more, the number of times $S_R < S_V$ was satisfied was completely 100. These results agreed with the results of the above-described surface plasmon resonance analysis of intermolecular interaction where the binding to HMGB1 was actually examined. In particular, by using the t test in combination, the results obtained regarding R4 became substantially 0. Thus, it can be said that it is possible to determine whether or not aptamer sequences that can bind to a target substance are enriched with high reliability, while avoiding the occurrence of false positive regarding R4. Also, since stable results were obtained when the number of samples was 40 or more, it can be said that, by setting the number of samples to at least 40, false negative determination can be avoided and the reliability can further be improved.

Furthermore, regarding the pool each round when the number of samples was 20, 40, 80, or 180, the standard deviation of the mean free energy is shown in Table 4 below.

TABLE 4

| | Standard deviation of mean free energy Number of samples | | | |
|---|---|---|---|---|
| Round | 20 | 40 | 80 | 180 |
| R1 | 0.7296 | 0.6492 | 0.4839 | 0.2842 |
| R2 | 0.8145 | 0.5586 | 0.4343 | 0.2601 |
| R3 | 0.8847 | 0.5837 | 0.4572 | 0.2992 |
| R4 | 0.7800 | 0.5629 | 0.4054 | 0.2773 |
| R5 | 1.0029 | 0.7364 | 0.4450 | 0.3301 |
| R6 | 0.9230 | 0.6966 | 0.4675 | 0.3305 |
| R7 | 0.7012 | 0.5965 | 0.3771 | 0.2489 |
| R8 | 0.5622 | 0.3199 | 0.2230 | 0.1759 |

As can be seen from Table 4, the standard deviation decreased in keeping with the increase in the number of samples. From this result, it can be said that, for example, by increasing the number of samples, determination with higher reliability becomes possible at any stage of the selection process.

Figure 10:
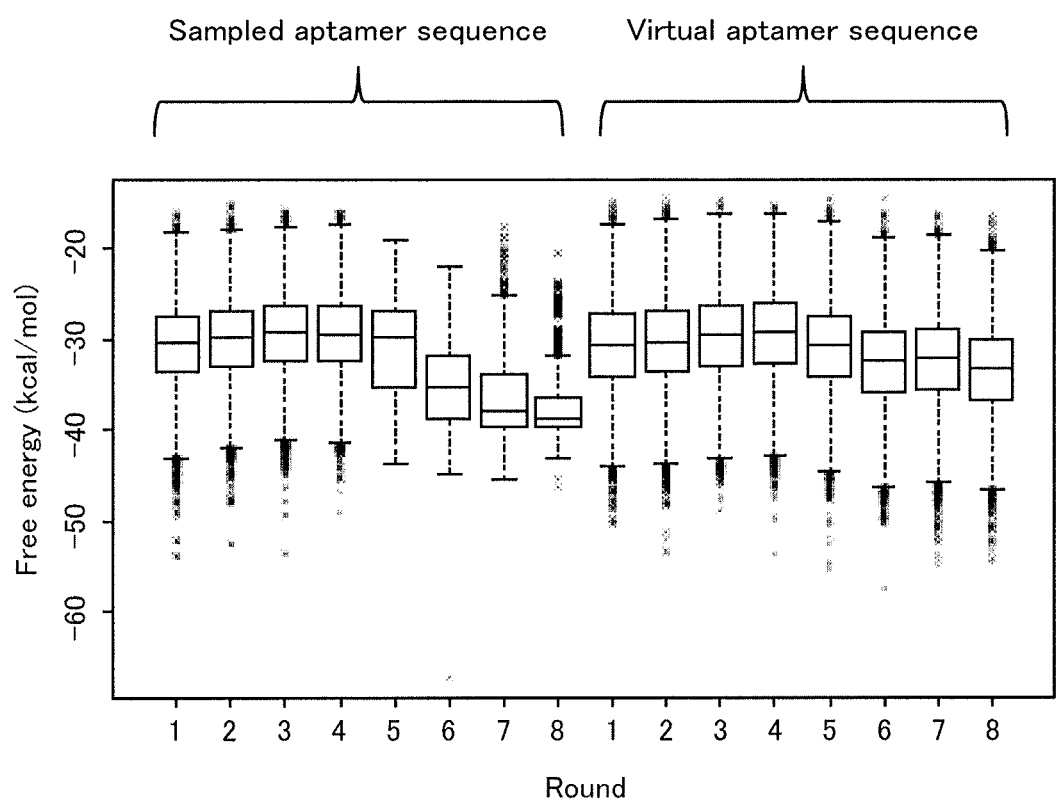
FIG. 10 is a graph showing the mean of free energies in a sampled aptamer sequence group and the mean of free energies in a virtual aptamer sequence group in Example 1 according to the present invention.

(1-3) Comparison Between Sampled Aptamer Sequences from Different Rounds and Comparison Between Sampled Aptamer Sequences and Virtual Aptamer Sequences Except that all the aptamer sequences contained in the pool of each round were set as sampled aptamer sequences in the pool, generation of 10000 virtual aptamer sequence and calculation of the mean of free energies of the sampled aptamer sequences and the means of free energies of the virtual aptamer sequence were carried out in the same manner as in the item (1-2) above. The results thereof are shown in the box plot of FIG. 10. In FIG. 10, the vertical axis indicates the free energy (unit kcal/mol), and the horizontal axis indicates the round (R1 to R8). In FIG. 10, the left half shows the results obtained regarding the sampled aptamer sequences, and the right half show the results obtained regarding the virtual aptamer sequences.

First, medians of the free energies of the sampled aptamer sequences of the respective rounds were compared with each other. As a result, the free energy decreased considerably in R6 and the rounds subsequent thereto, as compared with the degree of decrease in R1 to R5. As described above, R6 was found to be the round where the HMGB1-binding aptamers were enriched considerably. These results demonstrate that it is possible to check whether or not desired aptamers are enriched by checking the decrease in free energy.

Next, regarding each round, the median of the free energies of the sampled aptamer sequences was compared with that of the virtual aptamer sequences. As a result, it was found that, in R5, the median of the virtual aptamer sequence was smaller than that of the sampled aptamer sequences, and in R6 and the round subsequent thereto, the median of the virtual aptamer sequence was much lower than that of the sampled aptamer sequences. These results demonstrate that, by comparing the free energies of the sampled aptamer sequences with the free energies of the virtual aptamer sequences, it is possible to check whether or not the desired aptamers are enriched.

While the present invention has been described above with reference to illustrative embodiments, the present invention is by no means limited thereto. Various changes and modifications that may become apparent to those skilled in the art may be made in the configuration and specifics of the present invention without departing from the scope of the present invention.

This application claims priority from Japanese Patent Application No. 2010-152020 filed on Jul. 2, 2010. The entire disclosure of this Japanese patent application is incorporated herein by reference.

INDUSTRIAL APPLICABILITY

According to the present invention, it is possible to predict easily whether or not the desired aptamer sequences are enriched merely by comparing the free energy of the target aptamer sequence group with the free energy of the reference aptamer sequence group. Thus, according to the present invention, for example, it is possible to prevent the selection process for enriching the desired aptamers from being repeated excessively or the number of the selection rounds for enrichment from being insufficient. Moreover, by predicting whether or not the enrichment has been achieved according to the present invention, checking by a wet lab experiment needs to be performed only with respect to a pool for which such checking is considered to be necessary, resulting in reduction in labor and cost, for example.

EXPLANATION OF REFERENCE NUMERALS 10, 40, 50: prediction device
11: input unit
12: free energy calculation unit
13: enrichment prediction unit 14: output unit
15: data processing device
16: server
17: line network
41: sequence storage unit
42: free energy storage unit
43: storage device
54: virtual aptamer generation unit
111: communication interface

The invention claimed is:

1. A prediction device for predicting whether or not aptamers that bind to a desired target molecule are enriched in an aptamer pool, the prediction device comprising:
a processor;
memory storing executable instructions that, when executed by the processor, causes the processor to perform the steps of:
inputting sequence information on a target aptamer group and sequence information on a reference aptamer group,
wherein the target aptamer group sequence information has been obtained by sequencing aptamers from an aptamer pool containing a plurality of aptamers, wherein the aptamers in said plurality of aptamers each contain identical 3'-end primer-binding regions and identical 5'-end primer-binding regions, and each have an arbitrary region between their 3'-end primer-binding region and their 5'-end primer-binding region
wherein said aptamer pool has been obtained by enrichment with Systematic Evolution of Ligands by EXponential enrichment (SELEX), said SELEX enrichment comprising consecutive rounds of selection for RNA molecules that specifically bind ,to a desired target molecule, wherein the first selection round comprises contacting an RNA library comprising random sequences with the desired target molecule, and amplifying RNA molecules therefrom which specifically bind to the desired target molecule; and wherein subsequent rounds comprise contacting RNA molecules amplified from e previous round with the desired target molecule, and amplifying RNA molecules therefrom which specifically bind to the desired target molecule,
and wherein said reference aptamer group is a virtual aptamer group that includes virtual aptamer sequences, wherein the virtual aptamer sequences each contain identical 3'-end primer-binding regions and identical 5'-end primer-binding regions with the same sequence as the 3'- and 5'-end primer-binding regions of the aptamers in said target aptamer group, and each virtual aptamer sequence has an arbitrary region between its 3'-end primer-binding region and its 5'-end primer-binding region with the same base composition as the arbitrary region in the target aptamer group;
calculating a free energy of the target aptamer group based on the target aptamer group sequence information, and calculating a free energy of the reference aptamer group based on the reference aptamer group sequence information;
comparing the free energy of the target aptamer group with the free energy of the reference aptamer group; and
predicting that aptamers that bind to the desired target molecule are enriched in said aptamer pool when the free energy of the target aptamer group is lower than the free energy of the reference aptamer group.

2. The prediction device according to claim 1, wherein said memory stores further executable instructions that, when executed by the processor, cause the processor to perform the steps of:
generating the virtual aptamer sequences, said generating comprising generating virtual aptamer sequences which each contain identical 3'-end primer-binding regions and identical 5'-end primer-binding regions, and which each have an arbitrary region between their 3'-end primer-binding region and their 5'-end primer-binding region which has the same base composition as the arbitrary region in the target aptamer group.

3. The prediction device according to claim 1, wherein the number of sequences in the virtual aptamer group is from 100 to 10,000,000.

4. The prediction device according to claim 1, wherein the number of sequences in the target aptamer group is from 5 to 100,000,000.

5. The prediction device according to claim 1, wherein the free energy is at least one of a mean and a variance of free energies of the respective sequences.

6. The prediction device according to claim 1, wherein said memory stores further executable instructions that, when executed by the processor, cause the processor to output a prediction result based on the predicting.

7. The prediction device according to claim 1, wherein said memory stores further executable instructions that, when executed by the processor, cause the processor to perform the step of outputting the result to a display device.

* * * * *